(12) United States Patent
Barski et al.

(10) Patent No.: US 7,840,416 B2
(45) Date of Patent: Nov. 23, 2010

(54) NATURALLY EXPRESSED MEDICAL PROCEDURE DESCRIPTIONS GENERATED VIA SYNCHRONIZED DIAGRAMS AND MENUS

(75) Inventors: Conrad H. Barski, Minneapolis, MN (US); John M. Starmer, Minneapolis, MN (US); Ingrid R. Svensson, Plymouth, MN (US); Steven J. Swenson, Lakeville, MN (US); Robert A. Duke, Maplewood, MN (US); Stephen R. Claypool, Minneapolis, MN (US); Ying Ching Yu, Roseville, MN (US); Peter E. Crist, Rockford, MN (US); Linda R. Peitzman, Eden Prairie, MN (US); David A. Del Toro, Woodbury, MN (US)

(73) Assignee: ProVation Medical Inc., Minneapolis, MN (US)

( * ) Notice: Subject to any disclaimer, the term of this patent is extended or adjusted under 35 U.S.C. 154(b) by 1477 days.

(21) Appl. No.: 10/745,759

(22) Filed: Dec. 23, 2003

(65) Prior Publication Data
US 2005/0137907 A1    Jun. 23, 2005

(51) Int. Cl.
 *G06Q 50/00* (2006.01)
(52) U.S. Cl. ......................................................... 705/2
(58) Field of Classification Search .................. 705/2
See application file for complete search history.

(56) References Cited

U.S. PATENT DOCUMENTS

| | | | |
|---|---|---|---|
| 5,277,188 A | 1/1994 | Selker | |
| 5,659,742 A | 8/1997 | Beattie et al. | |
| 5,924,074 A | 7/1999 | Evans | |
| 5,974,389 A | 10/1999 | Clark et al. | |
| 6,039,688 A | 3/2000 | Douglas et al. | |
| 6,115,626 A | 9/2000 | Whayne et al. | |
| 6,263,330 B1 | 7/2001 | Bessette | |
| 6,306,087 B1 | 10/2001 | Barnhill et al. | |
| 6,308,171 B1 | 10/2001 | De La Huerga | |
| 6,347,329 B1 | 2/2002 | Evans | |
| 6,468,210 B1 | 10/2002 | Iliff | |
| 6,475,143 B2 | 11/2002 | Iliff | |
| 6,524,241 B2 | 2/2003 | Iliff | |
| 6,527,713 B2 | 3/2003 | Iliff | |
| 6,636,990 B1 | 10/2003 | Wadewitz | |

(Continued)

OTHER PUBLICATIONS

ProVation, Overview Brochure and Associated Articles, varying dates on or before the access date of Sep. 28, 2002.*

(Continued)

*Primary Examiner*—Luke Gilligan
*Assistant Examiner*—Robert Sorey
(74) *Attorney, Agent, or Firm*—Merchant & Gould P.C.

(57) ABSTRACT

A computing device-based system and method are described for generating a medical procedure description recorded into the system by a physician. The system and method manipulate a set of database records comprising medical content which is naturally descriptive of clinical procedures and clinically accurate diagrams which are naturally descriptive to document a medical procedure. To support the generation of a set of said medical procedure descriptions, the system and method provide interchangeable, connected, ontologically-based medical procedure database cartridges of medical content terms, rules, and diagrams that naturally describe constrained procedure representations for clinical procedure descriptions.

18 Claims, 42 Drawing Sheets

U.S. PATENT DOCUMENTS

| | | | |
|---|---|---|---|
| 6,736,776 B2 * | 5/2004 | Miles | 600/300 |
| 6,801,916 B2 | 10/2004 | Robergé et al. | |
| 7,343,305 B2 * | 3/2008 | Benn et al. | 705/3 |
| 2002/0028006 A1 | 3/2002 | Novak et al. | |
| 2002/0046346 A1 | 4/2002 | Evans | |
| 2002/0065854 A1 * | 5/2002 | Pressly | 707/530 |
| 2002/0082868 A1 * | 6/2002 | Pories et al. | 705/3 |
| 2002/0138306 A1 | 9/2002 | Sabovich | |
| 2002/0170565 A1 * | 11/2002 | Walker et al. | 128/920 |
| 2002/0172498 A1 | 11/2002 | Esenyan et al. | |
| 2002/0178032 A1 * | 11/2002 | Benn et al. | 705/2 |
| 2002/0194023 A1 * | 12/2002 | Turley et al. | 705/2 |
| 2003/0033169 A1 * | 2/2003 | Dew | 705/3 |
| 2003/0083903 A1 * | 5/2003 | Myers | 705/2 |
| 2003/0088441 A1 | 5/2003 | McNerney | |
| 2003/0154085 A1 | 8/2003 | Kelley | |
| 2004/0073092 A1 * | 4/2004 | Miles | 600/300 |
| 2004/0111296 A1 * | 6/2004 | Rosenfeld et al. | 705/2 |
| 2004/0260666 A1 | 12/2004 | Pestotnik et al. | |
| 2005/0027563 A1 * | 2/2005 | Fackler et al. | 705/2 |
| 2005/0075535 A1 * | 4/2005 | Shapiro et al. | 600/101 |
| 2005/0209880 A1 | 9/2005 | Drelicharz et al. | |

OTHER PUBLICATIONS

ProVation™ MD Clinical Productivity by Design™ Gastroenterology User Manual, Rev. 3.0, Jun. 2001, 245 pages.

ProVation™ MD Clinical Productivity by Design™ Gastroenterology User Manual, Rev. 3.5.1.8.7-03, Part No. 6016, May 2002, 259 pages.

Gamma et al., Design Patterns: Elements of Reusable Object-Oriented Software, 1994, 14 pages.

* cited by examiner

```
SCHEDULING
[icons: ERASE  SCHEDULE  NOTES  PRINT  EXIT]
☐ PATIENT - 777: LIPA, MARY M.
▽ CONSENT
   ☐ CONSENT O | — SPECIALTIES — | ☒
   ☐ PROCEDURE(S) | CARDIOLOGY CATH      ▷ | LEFT HEART CATH  ▷ | — LEFT HEART CATH —        | NY PATIENT.
                  | CARDIOLOGY ECHO      ▷ | RIGHT HEART CATH ▷ | CARDIAC CATH                | NOTHER PROCEDURE
                  | CARDIOLOGY NUCLEAR   ▷ |                    | PLACEMENT OF AORTIC BALLOON PUMP | CT THE PROCEDURE
                  | GI                   ▷ |                    | AORTOGRAPHY                 | FOR THE FIRST PROCEDURE.
                  | GENERAL SURGERY      ▷
                  | OB/GYN               ▷
                  | OPTHALMOLOGY/EYE     ▷
                  | ORTHOPEDICS          ▷
                  | OTOLARYNGOLOGY/ENT   ▷
                  | PAIN MANAGEMENT      ▷
                  | PULMONARY            ▷
                  | UROLOGY              ▷

◁  OCTOBER, 2003  ▷
SUN MON TUE WED THU FRI SAT
 28  29  30   1   2   3   4
  5   6  (7)  8   9  10  11
 12  13  14  15  16  17  18
 19  20  21  22  23  24  25
 26  27  28  29  30  31
     NOVEMBER, 2003
SUN MON TUE WED THU FRI SAT
                           1
  2   3   4   5   6   7   8
  9  10  11  12  13  14  15
 16  17  18  19  20  21  22
 23  24  25  26  27  28  29
 30   1   2   3   4   5   6
 ◯ TODAY: 10/7/2003
```

| DOCUMENTATION | |
|---|---|
| (icons) ERASE INSPECT NOTES PAST NOTES PRINT EXIT | EDIT  TOOL  PREFERENCE |
| | PROVATION MEDICAL CLINIC - WEST SITE (1) |

▼ NOTE RECORD
  □ MRN - 777
  □ PROC. DATE - 09/19/2003 15:05
  □ STATUS - OUTPATIENT
  □ ROOM # - SKIP
  □ CONSENT ON FILE - YES
▷ PROVIDER
  □ PROCEDURE
  □ PERTINENT MEDICATIONS
  □ PRE - PROCEDURE ASSESSMENT
  □ ADEQUACY/TOLERANCE
  □ INDICATIONS
  □ PATIENT HISTORY
  □ PROCEDURE MEDICATIONS
  □ DESCRIPTION OF PROCEDURE
  □ FINDING/INTERVENTIONS
  □ COMPLICATIONS
  □ IMPRESSION
  □ RECOMMENDATIONS
  □ POST CATH ORDERS
  □ PATIENT INSTRUCTIONS
  □ CODING

— 1901

MRN: 777                                    PROC. DATE: 09/19/2003 15:05
PATIENT NAME: LIPA, MARY M.                 AGE:

PROVIDER: DAVID A. DEL TORO MD (DOCTOR)
REFERRING MD:

[← — LEFT HEART CATH — ✖]
CARDIAC CATH
PLACEMENT OF AORTIC BALLOON PUMP
AORTOGRAPHY
— RIGHT HEART CATH —
RIGHT HEART CATHETERIZATION
PA CATHETER PLACEMENT (SWAN-GANZ)
PA ANGIOGRAM
ENDOMYOCARDIAL BIOPSY

ADEQUACY/TOLERANCE:

PROCEDURE MEDICATIONS:

DESCRIPTION OF PROCEDURE:

FINDINGS/INTERVENTIONS:

COMPLICATIONS:

IMPRESSION:

RECOMMENDATIONS:

POST CATH ORDERS:

PATIENT INSTRUCTIONS:

CPT4 CODE(S):

ICD9 CODE(S):

CC LETTER TO:

DOCUMENTATION

EDIT  TOOL  PREFERENCE

PROVATION MEDICAL CLINIC - WEST SITE (1)

- ▽ NOTE RECORD
  - ☐ MRN - 777
  - ☐ PROC. DATE - 09/19/2003 15:05
  - ☐ STATUS - OUTPATIENT
  - ☐ ROOM # - SKIP
  - ☐ CONSENT ON FILE - YES
- ▷ PROVIDER
- ☐ PROCEDURE
- ☐ PERTINENT MEDICATIONS
- ☐ PRE-PROCEDURE ASSESSMENT
- ☐ ADEQUACY/TOLERANCE
- ☐ INDICATIONS
- ☐ PATIENT HISTORY
- ☐ PROCEDURE MEDICATIONS
- ☐ DESCRIPTION OF PROCEDURE
- ☐ FINDING/INTERVENTIONS
- ☐ COMPLICATIONS
- ☐ IMPRESSION
- ☐ RECOMMENDATIONS
- ☐ POST CATH ORDERS
- ☐ PATIENT INSTRUCTIONS
- ☐ CODING

MRN: 777
PATIENT NAME: LIPA, MARY M.
PROC. DATE: 09/19/2003 15:05
AGE:

PROVIDER: DAVID A. DEL TORO MD (DOCTOR)  — 2101
REFERRING MD:

⎧ — LEFT HEART CATH —                          ☒
⎨ CARDIAC CATH
⎪ PLACEMENT OF AORTIC BALLOON PUMP
⎪ AORTOGRAPHY
⎪ — RIGHT HEART CATH —
⎪ RIGHT HEART CATHETERIZATION
⎪ PA CATHETER PLACEMENT (SWAN-GANZ)
⎪ PA ANGIOGRAM
⎩ ENDOMYOCARDIAL BIOPSY

⎫ 2100

ADEQUACY/TOLERANCE:

PROCEDURE MEDICATIONS:

DESCRIPTION OF PROCEDURE:

FINDINGS/INTERVENTIONS:

COMPLICATIONS:

IMPRESSION:

RECOMMENDATIONS:

POST CATH ORDERS:

PATIENT INSTRUCTIONS:

CPT4 CODE(S):

ICD9 CODE(S):

CC LETTER TO:

FIG. 21

| DOCUMENTATION | |
|---|---|
| [icons] ERASE INSPECT PAST NOTES PRINT EXIT | EDIT  TOOL  PREFERENCE |
| | PROVATION MEDICAL CLINIC - WEST SITE (1) |

▽ NOTE RECORD
   □ MRN - 777
   □ PROC. DATE - 10/23/2003 13:05
   □ STATUS - OUTPATIENT
   □ ROOM # - SKIP
   □ CONSENT ON FILE - YES
▷ PROVIDER
▽ PROCEDURE
   □ CARDIAC CATHETERIZATION
□ PERTINENT MEDICATIONS
□ PRE-PROCEDURE ASSESSMENT
□ ADEQUACY/TOLERANCE
□ INDICATIONS
□ PATIENT HISTORY
□ PROCEDURE MEDICATIONS
□ DESCRIPTION OF PROCEDURE
□ FINDING/INTERVENTIONS
□ COMPLICATIONS
□ IMPRESSION
□ RECOMMENDATIONS
□ POST CATH ORDERS
□ PATIENT INSTRUCTIONS
□ CODING

MRN: 777     PROC. DATE: 10/23/2003 13:05
PATIENT NAME: LIPA, MARY M.     AGE:

PROVIDER: DAVID A. DEL TORO MD (DOCTOR)
REFERRING MD:

PROCEDURE:
   CARDIAC CATHETERIZATION — 2200

INDICATIONS: — 2201

PATIENT HISTORY:

PERTINENT MEDICATIONS:

PRE-PROCEDURE ASSESSMENT:

ADEQUACY/TOLERANCE:

PROCEDURE MEDICATIONS:

DESCRIPTION OF PROCEDURE:

FINDINGS/INTERVENTIONS:

COMPLICATIONS:

IMPRESSION:

RECOMMENDATIONS:

POST CATH ORDERS:

PATIENT INSTRUCTIONS:

CPT4 CODE(S):

ICD9 CODE(S):

CC LETTER TO:

| DOCUMENTATION | |
|---|---|
| [icons] ERASE INSPECT NOTES PAST PRINT EXIT | EDIT  TOOL  PREFERENCE |
| | PROVATION MEDICAL CLINIC - WEST SITE (1) |

▽ NOTE RECORD
  ☐ MRN - 777
  ☐ PROC. DATE - 09/19/2003 15:05
  ☐ STATUS - OUTPATIENT
  ☐ ROOM # - SKIP
  ☐ CONSENT ON FILE - YES
▷ PROVIDER
▷ PROCEDURE
☐ PERTINENT MEDICATIONS
☐ PRE-PROCEDURE ASSESSMENT
☐ ADEQUACY/TOLERANCE
☐ INDICATIONS
☐ PATIENT HISTORY
☐ PROCEDURE MEDICATIONS
☐ DESCRIPTION OF PROCEDURE
☐ FINDING/INTERVENTIONS
☐ COMPLICATIONS
☐ IMPRESSION
☐ RECOMMENDATIONS
☐ POST CATH ORDERS
☐ PATIENT INSTRUCTIONS
☐ CODING

MRN: 777                          PROC. DATE: 09/19/2003 15:05
PATIENT NAME: LIPA, MARY M.        AGE:

PROVIDER: DAVID A. DEL TORO MD (DOCTOR)
REFERRING MD:

PROCEDURE:
  CARDIAC CATHETERIZATION
INDICATIONS:

PATIENT HISTORY:

PERTINENT MEDICATIONS:

PRE-PROCEDURE ASSESSMENT:

| DONE | ☒ |
| DIAGRAM DOCUMENTATION | | ← 2400
| ⊞ HEMODYNAMIC & OXYGEN DATA |
| ⊞ LEFT VENTRICULOGRAPHY |
| ⊞ SELECTIVE CORONARY ARTERIOGRAPHY |
| ⊞ SELECTIVE GRAFT VISUALIZATION |
|   ANGIOPLASTY |
|   STENT PLACEMENT |
|   ATHERECTOMY |
|   BRACHYTHERAPY |
|   THROMBECTOMY |
|   INTRACORONARY THROMBOLYTICS |
|   OTHER INTERVENTIONS |
|   CUSTOM |
|   GRAFT DESCRIPTION |

PATIENT INSTRUCTIONS:

CPT4 CODE(S):

ICD9 CODE(S):

CC LETTER TO:

| DOCUMENTATION | |
|---|---|
| ERASE INSPECT PAST PRINT EXIT NOTES | EDIT TOOL PREFERENCE |
| | PROVATION MEDICAL CLINIC - WEST SITE (1) |

| | |
|---|---|
| ▽ NOTE RECORD<br>   □ MRN - 777<br>   □ PROC. DATE - 09/19/2003 15:05<br>   □ STATUS - OUTPATIENT<br>   □ ROOM # - SKIP<br>   □ CONSENT ON FILE - YES<br>▷ PROVIDER<br>▷ PROCEDURE<br>□ PERTINENT MEDICATIONS<br>□ PRE - PROCEDURE ASSESSMENT<br>□ ADEQUACY/TOLERANCE<br>□ INDICATIONS<br>□ PATIENT HISTORY<br>□ PROCEDURE MEDICATIONS<br>□ DESCRIPTION OF PROCEDURE<br>▽ FINDING/INTERVENTIONS<br>  ▽ STENOSIS<br>    LOCATION - MID RCA<br>    DEGREE - 43%<br>    STENOSIS TYPE - DIFFUSE<br>    DESCRIPTION - ECCENTRIC<br>    THROMBUS - THROMBUS PRESENT<br>□ COMPLICATIONS<br>□ IMPRESSION<br>□ RECOMMENDATIONS<br>□ POST CATH ORDERS<br>□ PATIENT INSTRUCTIONS<br>□ CODING | MRN: 777          PROC. DATE: 09/19/2003 15:05<br>PATIENT NAME: LIPA, MARY M.    AGE:<br><br>PROVIDER: DAVID A. DEL TORO MD (DOCTOR)<br>REFERRING MD:<br><br>PROCEDURE:<br>   CARDIAC CATHETERIZATION<br>INDICATIONS:<br><br>PATIENT HISTORY:<br><br>PERTINENT MEDICATIONS:<br><br>PRE-PROCEDURE ASSESSMENT:<br><br>ADEQUACY/TOLERANCE:<br><br>PROCEDURE MEDICATIONS:    3200           3201<br>    IPTION OF PROCEDURE:<br><br>FINDINGS/INTERVENTIONS:<br>  SELECTIVE CORONARY ARTERIOGRAPHY:<br>    - THERE WAS A 43% DIFFUSE ECCENTRIC STENOSIS IN THE MID-RIGHT CORONARY ARTERY WITH THROMBUS PRESENT.<br><br>COMPLICATIONS:<br><br>IMPRESSION:<br><br>RECOMMENDATIONS:<br><br>POST CATH ORDERS:<br><br>PATIENT INSTRUCTIONS:<br><br>CPT4 CODE(S):<br><br>ICD9 CODE(S):<br><br>CC LETTER TO: |

FIG. 32

DOCUMENTATION

EDIT TOOL PREFERENCE

ERASE INSPECT NOTES PAST NOTES PRINT EXIT

PROVATION MEDICAL CLINIC - WEST SITE (1)

▽ NOTE RECORD
  ☐ MRN - 777
  ☐ PROC. DATE - 09/19/2003 15:05
  ☐ STATUS - OUTPATIENT
  ☐ ROOM # - SKIP
  ☐ CONSENT ON FILE - YES
▷ PROVIDER
▷ PROCEDURE
☐ PERTINENT MEDICATIONS
☐ PRE - PROCEDURE ASSESSMENT
☐ ADEQUACY/TOLERANCE
☐ INDICATIONS
☐ PATIENT HISTORY           3301
☐ PROCEDURE MEDICATIONS
☐ DESCRIPTION OF PROCEDURE
▽ FINDING/INTERVENTIONS
  ▽ STENOSIS
     LOCATION - MID RCA
     DEGREE - 43%
     STENOSIS TYPE - DIFFUSE
     DESCRIPTION - ECCENTRIC       3304
     THROMBUS - THROMBUS PRESENT
☐ COMPLICATIONS
☐ IMPRESSION
☐ RECOMMENDATIONS
☐ POST CATH ORDERS
☐ PATIENT INSTRUCTIONS
☐ CODING

MRN: 777                             PROC. DATE: 09/19/2003 15:05
PATIENT NAME: LIPA, MARY M.          AGE:

PROVIDER: DAVID A. DEL TORO MD (DOCTOR)
REFERRING MD:

PROCEDURE:
    CARDIAC CATHETERIZATION

INDICATIONS:

PATIENT HISTORY:

PERTINENT MEDICATIONS:

PRE-PROCEDURE ASSESSMENT:

DONE                                          ✖
DIAGRAM DOCUMENTATION
⊞ HEMODYNAMIC & OXYGEN DATA
⊞ LEFT VENTRICULOGRAPHY
   SELECTIVE CORONARY ARTERIOGRAPHY
      LEFT MAIN CORONARY ARTERY        ▷
      INTERMEDIATE RAMUS OF LCA        ▷
      LATERAL SUB-BRANCH               ▷
      LEFT ANTERIOR DESCENDING ARTERY  ▷  MID-RIGHT CORONARY ARTERY, WITH THROMBUS PRESENT.
      DIAGONAL BRANCHES OF LAD         ▷
      SEPTAL PERFORATOR OF LAD         ▷
      LEFT CIRCUMFLEX CORONARY ARTERY  ▷
      OBTUSE MARGINAL BRANCH OF CX     ▷
      POSTEROLATERAL BRANCHES OF CX    ▷
      DOMINANT CX-POSTERIOR DESCENDING BR. ▷
      AV CONTINUATION SEGMENT          ▷
      RIGHT CORONARY ARTERY            ▷
      ACUTE MARGINAL BRANCH OF RCA     ▷
      POSTERIOR DESCENDING BRANCH OF RCA ▷     ⎬ 3302
      POSTEROLATERAL SEGMENT OF RCA    ▷
      POSTERIOR ATRIOVENTRICULAR SEGMENT ▷
      SEPTAL PERFORATOR OF PDA BRANCH  ▷
   NEW FINDINGS MENU
      STENOSIS
3303 ⊞ SELECTIVE GRAFT VISUALIZATION
      ANGIOPLASTY
      STENT PLACEMENT
      ATHERECTOMY
      BRACHYTHERAPY
      THROMBECTOMY
      INTRACORONARY THROMBOLYTICS
      OTHER INTERVENTIONS
      CUSTOM
      GRAFT DESCRIPTION

| DOCUMENTATION | |
|---|---|
| [icons] ERASE INSPECT PAST NOTES PRINT EXIT | EDIT  TOOL  PREFERENCE |
| | PROVATION MEDICAL CLINIC - WEST SITE (1) |
| ▼ NOTE RECORD<br>　☐ MRN - 777<br>　☐ PROC. DATE - 09/19/2003 15:05<br>　☐ STATUS - OUTPATIENT<br>　☐ ROOM # - SKIP<br>　☐ CONSENT ON FILE - YES<br>▷ PROVIDER<br>▷ PROCEDURE<br>☐ PERTINENT MEDICATIONS<br>☐ PRE - PROCEDURE ASSESSMENT<br>☐ ADEQUACY/TOLERANCE<br>☐ INDICATIONS<br>☐ PATIENT HISTORY<br>☐ PROCEDURE MEDICATIONS<br>☐ DESCRIPTION OF PROCEDURE<br>▼ FINDING/INTERVENTIONS<br>　▼ STENOSIS<br>　　LOCATION - MID RCA<br>　　DEGREE - 43%<br>　　STENOSIS TYPE - DIFFUSE<br>　　DESCRIPTION - ECCENTRIC<br>　　THROMBUS - THROMBUS PRESENT<br>　▼ STENOSIS<br>　　LOCATION - MID - LAD ARTERY<br>　　DEGREE - 44%<br>　　STENOSIS TYPE -<br>　　DESCRIPTION -<br>　　THROMBUS -<br>☐ COMPLICATIONS<br>☐ IMPRESSION<br>☐ RECOMMENDATIONS<br>☐ POST CATH ORDERS<br>☐ PATIENT INSTRUCTIONS<br>☐ CODING | MRN: 777　　　　　　　　　　PROC. DATE: 09/19/2003 15:05<br>PATIENT NAME: LIPA, MARY M.　　AGE:<br><br>PROVIDER: DAVID A. DEL TORO MD (DOCTOR)<br>REFERRING MD:<br>――――――――――――――――――<br>PROCEDURE:<br>　CARDIAC CATHETERIZATION<br>INDICATIONS:<br><br>PATIENT HISTORY:<br><br>PERTINENT MEDICATIONS:<br><br>PRE-PROCEDURE ASSESSMENT:<br><br>ADEQUACY/TOLERANCE:<br>――――――――――――――――――<br>PROCEDURE MEDICATIONS:<br><br>DESCRIPTION OF PROCEDURE:<br><br>FINDINGS/INTERVENTIONS:<br>SELECTIVE CORONARY ARTERIOGRAPHY:<br>[← DISCRETE ✕]  3% DIFFUSE ECCENTRIC STENOSIS IN THE MID-RIGHT CORONARY ARTERY, WITH THROMBUS<br>　DIFFUSE　　[TYPE][DESCRIPTION] STENOSIS IN THE MID-LEFT ANTERIOR DESCENDING ARTERY [THROMBUS].<br>　LONG<br><br>IMPRESSION:<br><br>RECOMMENDATIONS:<br><br>POST CATH ORDERS:<br><br>PATIENT INSTRUCTIONS:<br><br>CPT4 CODE(S):<br><br>ICD9 CODE(S):<br><br>CC LETTER TO: |

Callouts: 3600, 3602, 3604, 3603

FIG. 36

| DOCUMENTATION | |
|---|---|
| ERASE INSPECT PAST NOTES PRINT EXIT | EDIT TOOL PREFERENCE |
| | PROVATION MEDICAL CLINIC - WEST SITE (1) |
| ▽ NOTE RECORD<br>□ MRN - 777<br>□ PROC. DATE - 09/19/2003 15:05<br>□ STATUS - OUTPATIENT<br>□ ROOM # - SKIP<br>□ CONSENT ON FILE -YES<br>▷ PROVIDER<br>▷ PROCEDURE<br>□ PERTINENT MEDICATIONS<br>□ PRE - PROCEDURE ASSESSMENT<br>□ ADEQUACY/TOLERANCE<br>□ INDICATIONS<br>□ PATIENT HISTORY<br>□ PROCEDURE MEDICATIONS<br>□ DESCRIPTION OF PROCEDURE<br>▽ FINDING/INTERVENTIONS<br>  ▽ STENOSIS<br>    LOCATION - MID RCA<br>    DEGREE - 43%<br>    STENOSIS TYPE - DIFFUSE<br>    DESCRIPTION - ECCENTRIC<br>    THROMBUS - THROMBUS PRESENT<br>  ▽ STENOSIS  3700<br>    LOCATION - MID -LAD ARTERY<br>    DEGREE - 44%<br>    STENOSIS TYPE - DISCRETE<br>    DESCRIPTION -<br>    THROMBUS -<br>□ COMPLICATIONS<br>□ IMPRESSION<br>□ RECOMMENDATIONS  3704<br>□ POST CATH ORDERS<br>□ PATIENT INSTRUCTIONS<br>□ CODING | MRN: 777    PROC. DATE: 09/19/2003 15:05<br>PATIENT NAME: LIPA, MARY M.    AGE:<br>PROVIDER: DAVID A. DEL TORO MD (DOCTOR)<br>REFERRING MD:<br>PROCEDURE:<br>   CARDIAC CATHETERIZATION<br>INDICATIONS:<br>PATIENT HISTORY:<br>PERTINENT MEDICATIONS:<br>PRE-PROCEDURE ASSESSMENT:<br>ADEQUACY/TOLERANCE:<br><br>PROCEDURE MEDICATIONS:<br>DESCRIPTION OF PROCEDURE:<br>FINDINGS/INTERVENTIONS:<br>SELECTIVE CORONARY ARTERIOGRAPHY:<br>- THERE WAS A 43% DIFFUSE ECCENTRIC STENOSIS IN THE MID-RIGHT CORONARY ARTERY, WITH THROMBUS PRESENT. THERE WAS A 44% DESCRETE [DESCRIPTION] STENOSIS IN THE MID-LEFT ANTERIOR DESCENDING ARTERY [THROMBUS].<br><br>[DONE] [X]<br>CONCENTRIC<br>ECCENTRIC<br>CALCIFIED<br>HAZY LESION<br>IRREGULAR<br>TUBULAR<br>ULCERATED<br><br>CPT4 CODE(S):<br>ICD9 CODE(S):<br>CC LETTER TO: |

FIG. 37

| DOCUMENTATION | |
|---|---|
| ERASE INSPECT PAST PRINT EXIT NOTES | EDIT  TOOL  PREFERENCE |
| | PROVATION MEDICAL CLINIC - WEST SITE (1) |

| | |
|---|---|
| ▽ NOTE RECORD<br>　□ MRN - 777<br>　□ PROC. DATE - 09/19/2003 15:05<br>　□ STATUS - OUTPATIENT<br>　□ ROOM # - SKIP<br>　□ CONSENT ON FILE - YES<br>▷ PROVIDER<br>▷ PROCEDURE<br>　□ PERTINENT MEDICATIONS<br>　□ PRE - PROCEDURE ASSESSMENT<br>　□ ADEQUACY/TOLERANCE<br>□ INDICATIONS<br>□ PATIENT HISTORY<br>□ PROCEDURE MEDICATIONS<br>□ DESCRIPTION OF PROCEDURE<br>▽ FINDING/INTERVENTIONS<br>　▽ STENOSIS<br>　　LOCATION - MID RCA<br>　　DEGREE - 43%<br>　　STENOSIS TYPE - DIFFUSE<br>　　DESCRIPTION - ECCENTRIC<br>　　THROMBUS - THROMBUS PRESENT<br>　▽ STENOSIS<br>　　LOCATION - MID -LAD ARTERY<br>　　DEGREE - 44%　　3800<br>　　STENOSIS TYPE - DISCRETE<br>　　DESCRIPTION - ECCENTRIC<br>　　THROMBUS -<br>□ COMPLICATIONS<br>□ IMPRESSION　3804<br>□ RECOMMENDATIONS<br>□ POST CATH ORDERS<br>□ PATIENT INSTRUCTIONS<br>□ CODING | MRN: 777　　　　　　PROC. DATE: 09/19/2003 15:05<br>PATIENT NAME: LIPA, MARY M.　　AGE:<br><br>PROVIDER: DAVID A. DEL TORO MD (DOCTOR)<br>REFERRING MD:<br>PROCEDURE:<br>　CARDIAC CATHETERIZATION<br>INDICATIONS:<br><br>PATIENT HISTORY:<br><br>PERTINENT MEDICATIONS:<br><br>PRE-PROCEDURE ASSESSMENT:<br><br>ADEQUACY/TOLERANCE:<br><br>PROCEDURE MEDICATIONS:<br><br>DESCRIPTION OF PROCEDURE:<br><br>FINDINGS/INTERVENTIONS:<br><br>SELECTIVE CORONARY ARTERIOGRAPHY:<br>- THERE WAS A 43% DIFFUSE ECCENTRIC STENOSIS IN THE MID-RIGHT CORONARY ARTERY, WITH THROMBUS PRESENT. THERE WAS A 44% DESCRETE ECCENTRIC STENOSIS IN THE MID-LEFT ANTERIOR DESCENDING ARTERY [THROMBUS].　　　　　　}—3803<br><br>[←]—THROMBUS PRESENT—[✖]<br>　SKIP<br>　YES　　　　}3802<br>　NO<br><br>RECOMMENDATIONS:<br><br>POST CATH ORDERS:<br><br>PATIENT INSTRUCTIONS:<br><br>CPT4 CODE(S):<br><br>ICD9 CODE(S):<br><br>CC LETTER TO: |

FIG. 38

| DOCUMENTATION | |
|---|---|
| ERASE INSPECT PAST NOTES PRINT EXIT | EDIT  TOOL  PREFERENCE |
| | PROVATION MEDICAL CLINIC - WEST SITE (1) |

| ▽ NOTE RECORD<br>    ▫ MRN - 777<br>    ▫ PROC. DATE - 09/19/2003 15:05<br>    ▫ STATUS - OUTPATIENT<br>    ▫ ROOM # - SKIP<br>    ▫ CONSENT ON FILE - YES<br>▷ PROVIDER<br>▷ PROCEDURE<br>▫ PERTINENT MEDICATIONS<br>▫ PRE - PROCEDURE ASSESSMENT<br>▫ ADEQUACY/TOLERANCE<br>▫ INDICATIONS<br>▫ PATIENT HISTORY<br>▫ PROCEDURE MEDICATIONS<br>▫ DESCRIPTION OF PROCEDURE<br>▽ FINDING/INTERVENTIONS<br>  ▽ STENOSIS<br>    LOCATION - MID RCA<br>    DEGREE - 43%<br>    STENOSIS TYPE - DIFFUSE<br>    DESCRIPTION - ECCENTRIC<br>    THROMBUS - THROMBUS PRESENT<br>  ▽ STENOSIS<br>    LOCATION - MID -LAD ARTERY<br>    DEGREE - 44%<br>    STENOSIS TYPE - DISCRETE<br>    DESCRIPTION - ECCENTRIC<br>    THROMBUS - THROMBUS PRESENT<br>▫ COMPLICATIONS<br>▫ IMPRESSION<br>▫ RECOMMENDATIONS   3900<br>▫ POST CATH ORDERS<br>▫ PATIENT INSTRUCTIONS<br>▫ CODING | MRN: 777        PROC. DATE: 09/19/2003 15:05<br>PATIENT NAME: LIPA, MARY M.     AGE:<br><br>PROVIDER: DAVID A. DEL TORO MD (DOCTOR)<br>REFERRING MD:<br><br>PROCEDURE:<br>    CARDIAC CATHETERIZATION<br>INDICATIONS:<br><br>PATIENT HISTORY:<br><br>PERTINENT MEDICATIONS:<br><br>PRE-PROCEDURE ASSESSMENT:<br><br>ADEQUACY/TOLERANCE:<br><br>PROCEDURE MEDICATIONS:<br><br>DESCRIPTION OF PROCEDURE:<br><br>3901 INTERVENTIONS:<br><br>SELECTIVE CORONARY ARTERIOGRAPHY:<br>--THERE WAS A 43% DIFFUSE ECCENTRIC STENOSIS IN THE MID-RIGHT CORONARY ARTERY, WITH THROMBUS PRESENT. THERE WAS A 44% DESCRETE ECCENTRIC STENOSIS IN THE MID-LEFT ANTERIOR DESCENDING ARTERY WITH THROMBUS PRESENT.     — 3902<br>COMPLICATIONS:<br><br>IMPRESSION:<br><br>RECOMMENDATIONS:<br><br>POST CATH ORDERS:<br><br>PATIENT INSTRUCTIONS:<br><br>CPT4 CODE(S):<br><br>ICD9 CODE(S):<br><br>CC LETTER TO: |

FIG. 39

DOCUMENTATION

EDIT TOOL PREFERENCE

ERASE INSPECT PAST NOTES PRINT EXIT

PROVATION MEDICAL CLINIC - WEST SITE (1)

▼ NOTE RECORD
   ☐ MRN - 777
   ☐ PROC. DATE - 09/19/2003 15:05
   ☐ STATUS - OUTPATIENT
   ☐ ROOM # - SKIP
   ☐ CONSENT ON FILE - YES
▷ PROVIDER
▷ PROCEDURE
☐ PERTINENT MEDICATIONS
☐ PRE - PROCEDURE ASSESSMENT
☐ ADEQUACY/TOLERANCE
☐ INDICATIONS
☐ PATIENT HISTORY
☐ PROCEDURE MEDICATIONS
☐ DESCRIPTION OF PROCEDURE
▼ FINDING/INTERVENTIONS
  ▼ STENOSIS
    LOCATION - MID RCA
    DEGREE - 43%
    STENOSIS TYPE - DIFFUSE
    DESCRIPTION - ECCENTRIC
    THROMBUS - THROMBUS PRESENT
  ▼ STENOSIS
    LOCATION - MID -LAD ARTERY
    DEGREE - 44%
    STENOSIS TYPE - DISCRETE
    DESCRIPTION - ECCENTRIC
    THROMBUS - THROMBUS PRESENT
☐ COMPLICATIONS
☐ IMPRESSION
☐ RECOMMENDATIONS
☐ POST CATH ORDERS
☐ PATIENT INSTRUCTIONS
☐ CODING

MRN: 777        PROC. DATE: 09/19/2003 15:05
PATIENT NAME: LIPA, MARY M.    AGE:

PROVIDER: DAVID A. DEL TORO MD (DOCTOR)
REFERRING MD:

PROCEDURE:
   CARDIAC CATHETERIZATION

INDICATIONS:

PATIENT HISTORY:

PERTINENT MEDICATIONS:

PRE-PROCEDURE ASSESSMENT:

⬅ DONE         ✖  —4002
DIAGRAM DOCUMENTATION
⊞ HEMODYNAMIC & OXYGEN DATA
⊞ LEFT VENTRICULOGRAPHY
⊞ SELECTIVE CORONARY ARTERIOGRAPHY
⊞ SELECTIVE GRAFT VISUALIZATION

ANGIOPLASTY
4000 PLACEMENT
ATHERECTOMY
BRACHYTHERAPY   M D-RIGHT CORONARY ARTERY, WITH THROMBUS PRESENT. THERE WAS A
THROMBECTOMY    DESCENDING ARTERY WITH THROMBUS PRESENT.
INTRACORONARY THROMBOLYTICS
OTHER INTERVENTIONS
CUSTOM
GRAFT DESCRIPTION

}—4001

RECOMMENDATIONS:

POST CATH ORDERS:

PATIENT INSTRUCTIONS:

CPT4 CODE(S):

ICD9 CODE(S):

CC LETTER TO:

NATURALLY EXPRESSED MEDICAL PROCEDURE DESCRIPTIONS GENERATED VIA SYNCHRONIZED DIAGRAMS AND MENUS

FIELD OF THE INVENTION

The field of the present invention generally relates to systems and methods for medical procedure documentation, and in particular to a system and method for generating naturally expressed medical procedure descriptions via a synchronized diagram and menu system.

BACKGROUND OF THE INVENTION

The invention generally relates to graphical user interfaces, and more particularly to a graphical user interface used by physicians to quickly and concisely document procedures and/or exams conducted in healthcare facilities.

The development of graphical user interfaces started in the development labs of Xerox, IBM, and others and eventually made it to the public domain via the introduction of the Apple LISA personal computer, X-Windows on Unix terminals, TopView from IBM, and Windows from Microsoft. As the graphical user interface established itself as the primary means of computer to human interfacing there have been various methods seeking to improve the look, the feel, and the speed at which information is transferred from the end user to the software application and database operating under a graphical user interface. The present invention serves to improve upon these already developed methods by tying together methods that have been heretofore not engineered in a way the benefits the physician during their documentation of medical procedures and exams. The traditional method of physician medical procedure documentation is via the dictation and transcription model. Several vendors have developed structured methods of medical procedure documentation that are based on menus and menu trees. Other structured methods have been based on anatomic diagrams and annotating diagrams with text that documents findings, intervention, and maneuvers conducted during the medical procedure. A structured language bridge or ontology does not exist that uniquely matches up the documentation conducted via the menu method and the diagram method.

The invention allows the physician to generate naturally expressed medical procedure descriptions via a synchronized diagram and menu system. The physician is free to choose either method of documentation, either via a diagram or via a menu system. Entries or changes in one method of documentation are automatically synchronized with the other. This enables the physician to quickly and concisely generate naturally expressed medical procedure descriptions in a method that suits their needs.

There are systems and methods that address these issues. However, the prior art does not sufficiently address the issue of providing an efficient and effective means to solve these problems. There are several software systems in the public domain that allow for the entry of information via a menu system and several software systems that allow documentation and annotations to be completed via a diagram but none of the prior art brings these two methods together in a synchronized manner.

It would therefore be advantageous to have a method and system for designing and implementing a system and method for generating naturally expressed medical procedure descriptions via a synchronized diagram and menu system. In this manner, physicians are able to describe their procedures in a clinical style that is natural to the physician with alternative user interface methods that allows for the rapid entry of concise and complete medical procedure documentation.

The object of the invention is to provide a concise and complete procedure documentation system that generates naturally expressed medical procedure descriptions by allowing the physician to work with a user interface that is consistent with their style of documentation for their medical specialty. For example, cardiologists typically utilize pictures to describe their findings when speaking with the patient's family in the waiting room. The physician draws a heart showing the patient's family the findings and interventions that they encountered during the procedure. Afterward, the physician has to dictate their note and wait for the transcription to return before they are "completed" with the procedure. With the invention in place, the physician can utilize the diagram documentation method and use these diagrams as part of the procedure description and also use the diagrams to show the patient's family the findings and interventions.

It is another objective of the invention to keep the two methods of documentation synchronized to ensure that the documentation is correct independent of the method of data entry. The synchronization will additionally help to reduce medical errors. For example, the physician could document their procedure completely by using the diagrams and the documentation generated by the invention would have all of the information necessary to correctly assign the CPT and ICD9 codes associated with the medical procedure. Alternatively, the physician could document their procedure completely by using the menuing system and the documentation generated by the invention would have all of the information necessary to correctly assign the CPT and ICD9 codes associated with the medical procedure. The physician could choose to use either method during the procedure documentation process and the invention would keep the data synchronized.

Thus, as will be appreciated from a review of the drawings and detailed descriptions of the preferred embodiments, the present invention overcomes the significant limitations and shortcomings of the prior art.

SUMMARY OF THE INVENTION

The benefits of this invention will become clear and will be best appreciated with reference to the detailed description of the preferred embodiments. Other objects, advantages, and novel features will be apparent from the description when read in conjunction with the appended claims and attached drawings.

The present invention is an automated medical procedure documentation method utilizing a synchronized menu and diagramming system to generate the naturally expressed medical procedure descriptions.

A computer based system and method are described for generating naturally expressed medical procedure descriptions via a synchronized diagram and menu system which concisely and completely summarizes a clinical procedure description recorded into the system by a physician. The system and method manipulate a set of database records comprising medical content, such as procedure descriptions and medical diagrams which are naturally descriptive of clinical procedures.

The system provides the features that eliminate the error prone process of dictation and the often lengthy delays associated with transcribing, reviewing, recreating, and approving transcripts. Additionally, the system provides a diagram that can be used in a natural way to describe the findings, interventions, etc. that are part of the medical procedure. A minimal learning curve is required to become productive when using the invention.

The system's document driven charge capture module completes the process by transferring the documentation to the healthcare facilities billing system.

The present invention is a software program operating on a single general purpose computing device or a plurality of computing devices interconnected via a network system. The procedure documentation is readily available for review, print, fax, email operations.

The invention interface comprises a set of procedure descriptors designed as anticipatory driven drop down menus that controls the information input by a physician to document a medical procedure and an interface that allows for a simple interaction between a diagram and icons that represent, for example, various procedure or exam based findings, maneuvers, and interventions. The invention uses an anticipatory menu physician interface, which emulates a typical procedural workflow and a clinician's thought processes, instantly and automatically adapting to each piece of information that is input by the physician with a corresponding anatomic diagram that is tied to the procedure being documented.

A procedure description narrative is constructed based on the initial procedure category selected by a physician. As the physician documents the procedure using the anticipatory interface menus, the narrative is edited as the next procedure description item is selected from a next menu in the documentation process. While the physician is documenting the procedure using the anticipatory interface menus, a concurrent process is taking place that creates the synchronized diagram for printing, review, or editing. At the completion of the procedure documentation process, the procedure description narrative is completed and its description fields are filled in. The system reduces the time spent by the physician paging through a maze of screens to find the correct place to record information. The system also reduces the time spent by the physician scrolling through dozens of pull-down menus or the time spent by the physician reading through endless lists of words in search for terminology appropriate for the procedure at hand. The system reduces the time spent by the physician in documenting their procedure description by allowing the physician to document via a method that is more intuitive to their style.

Alternatively, the physician can invoke the diagram method of documentation and be presented with a diagram that presents the anatomy of the patient specific to the procedure being documented with icons representing various maneuvers, findings, and interventions. Certain elements of the diagram method are better represented with menus and thus the menu system is invoked to augment the diagram method of generating naturally expressed medical procedure descriptions.

BRIEF DESCRIPTION OF THE DRAWINGS

The present invention can be better understood with reference to the following diagrams. The components within the drawings are not necessarily to scale relative to each other, emphasis instead being placed upon clearly illustrating the principles of the present invention.

FIG. 17 is a screen shot illustrating the scheduling component of the system.

FIG. 19 is a screen shot illustrating the system's physician interface prompting the physician for the procedure name for the procedure that is requiring documentation.

FIG. 21 is a screen shot illustrating the system's physician interface prompting the physician to select a procedure that is requiring documentation.

FIG. 22 is a screen shot illustrating the system's physician interface after the physician has selected a procedure.

FIG. 23 is a screen shot illustrating the system's physician interface prompting the physician for the next attribute for the procedure that is requiring documentation.

FIG. 24 is a screen shot illustrating the system's physician interface which displays the finding menu with the Diagram Documentation menu selection.

FIG. 30 is a screen shot illustrating the system's diagramming physician interface requiring additional data entry for the procedure.

FIG. 32 is a screen shot illustrating the system's physician interface after returning from the diagramming physician's user interface.

FIG. 33 is a screen shot illustrating the system's physician interface requiring additional data entry for the procedure.

FIG. 34 is a screen shot illustrating the system's physician interface requiring additional data entry for the procedure.

FIG. 35 is a screen shot illustrating the system's physician interface requiring additional data entry for the procedure.

FIG. 36 is a screen shot illustrating the system's physician interface requiring additional data entry for the procedure.

FIG. 37 is a screen shot illustrating the system's physician interface requiring additional data entry for the procedure.

FIG. 38 is a screen shot illustrating the system's physician interface requiring additional data entry for the procedure.

FIG. 39 is a screen shot illustrating the system's physician interface after two stenosis have been documented via the menuing system FIG. 40 is a screen shot illustrating the system's physician interface which displays the finding menu with the Diagram Documentation menu selection.

FIG. 42 is a screen shot illustrating the system's diagramming physician interface for the diagram documentation related to Echocardiography.

DETAILED DESCRIPTION

Figure 1:
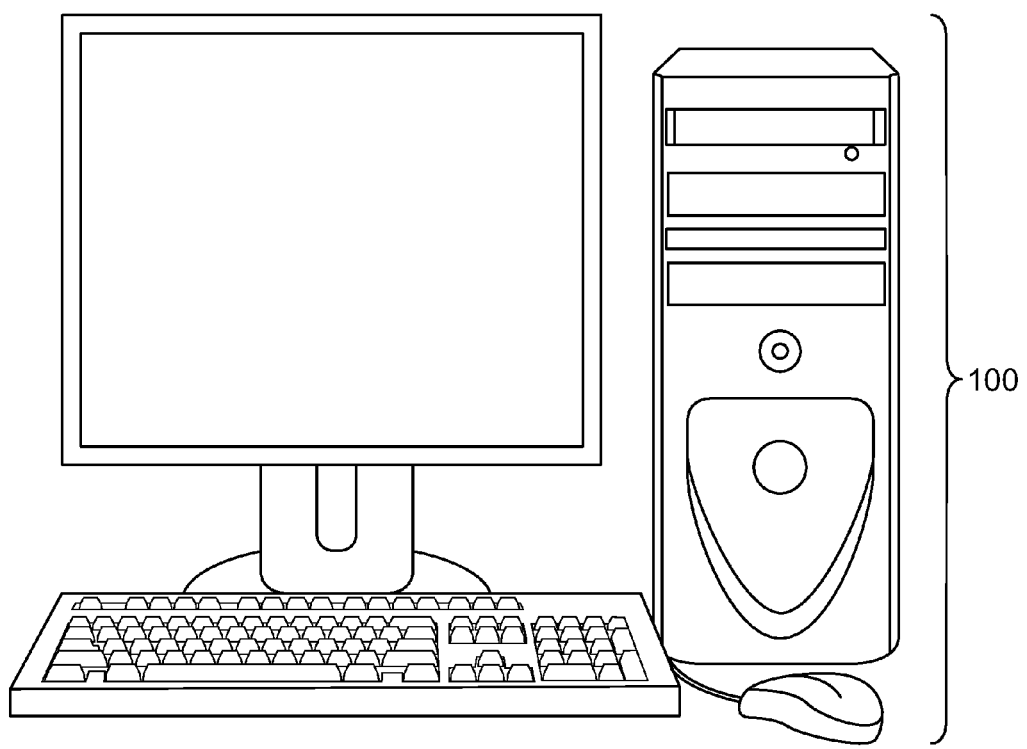
FIG. 1 is a graphical view illustrating a computing device called a personal computing device.
Figure 2:
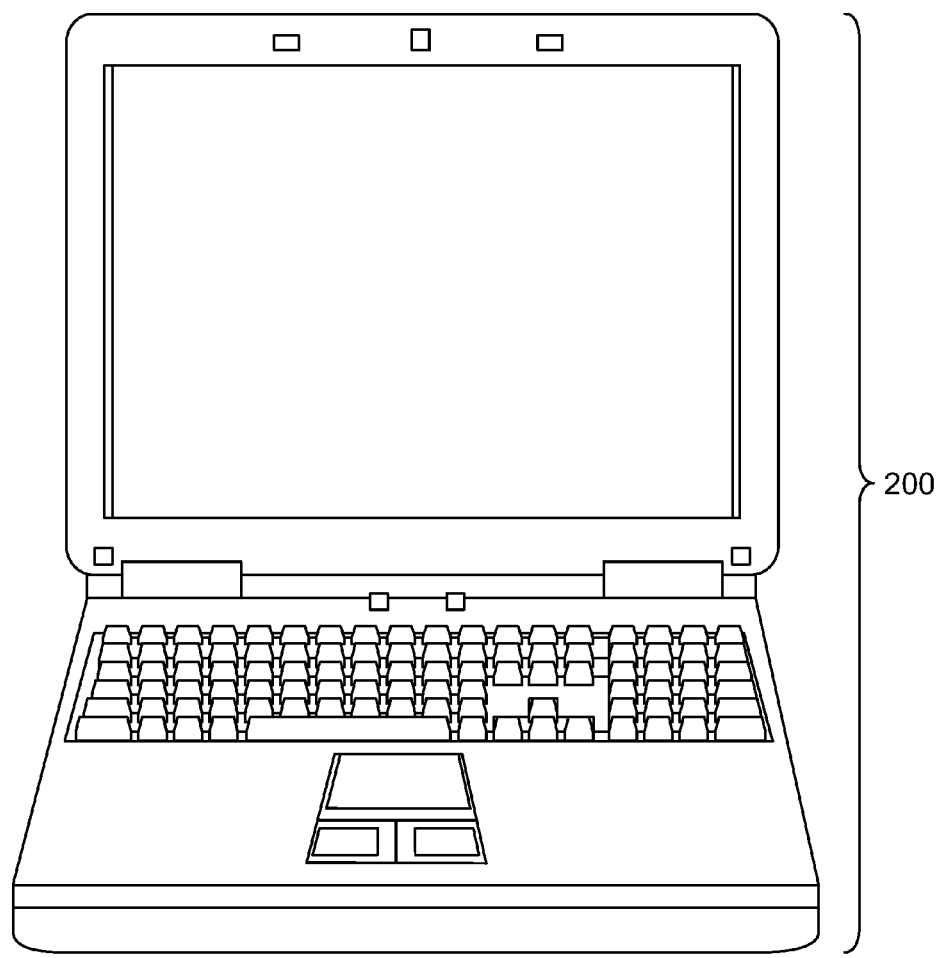
FIG. 2 is a graphical view illustrating a computing device called a laptop computing device.
Figure 3:
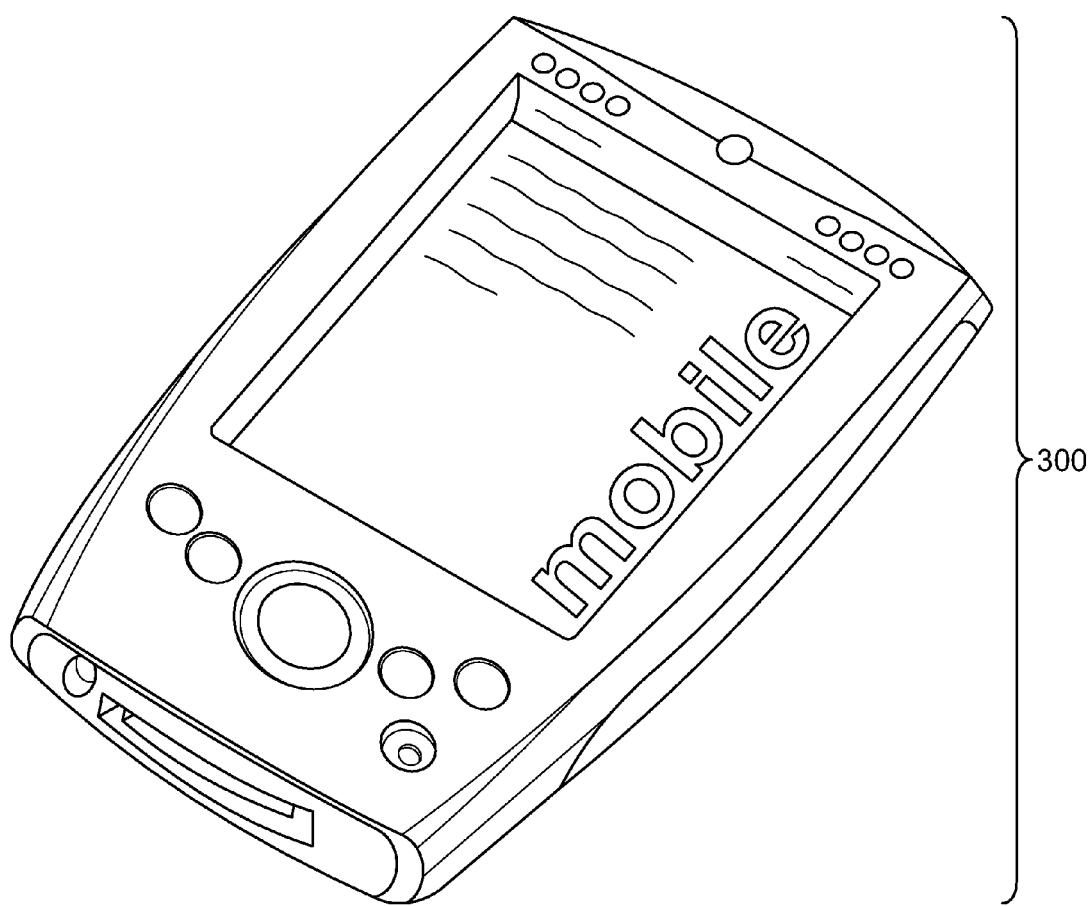
FIG. 3 is a graphical view illustrating a computing device called a personal digital assistant.
Figure 4:
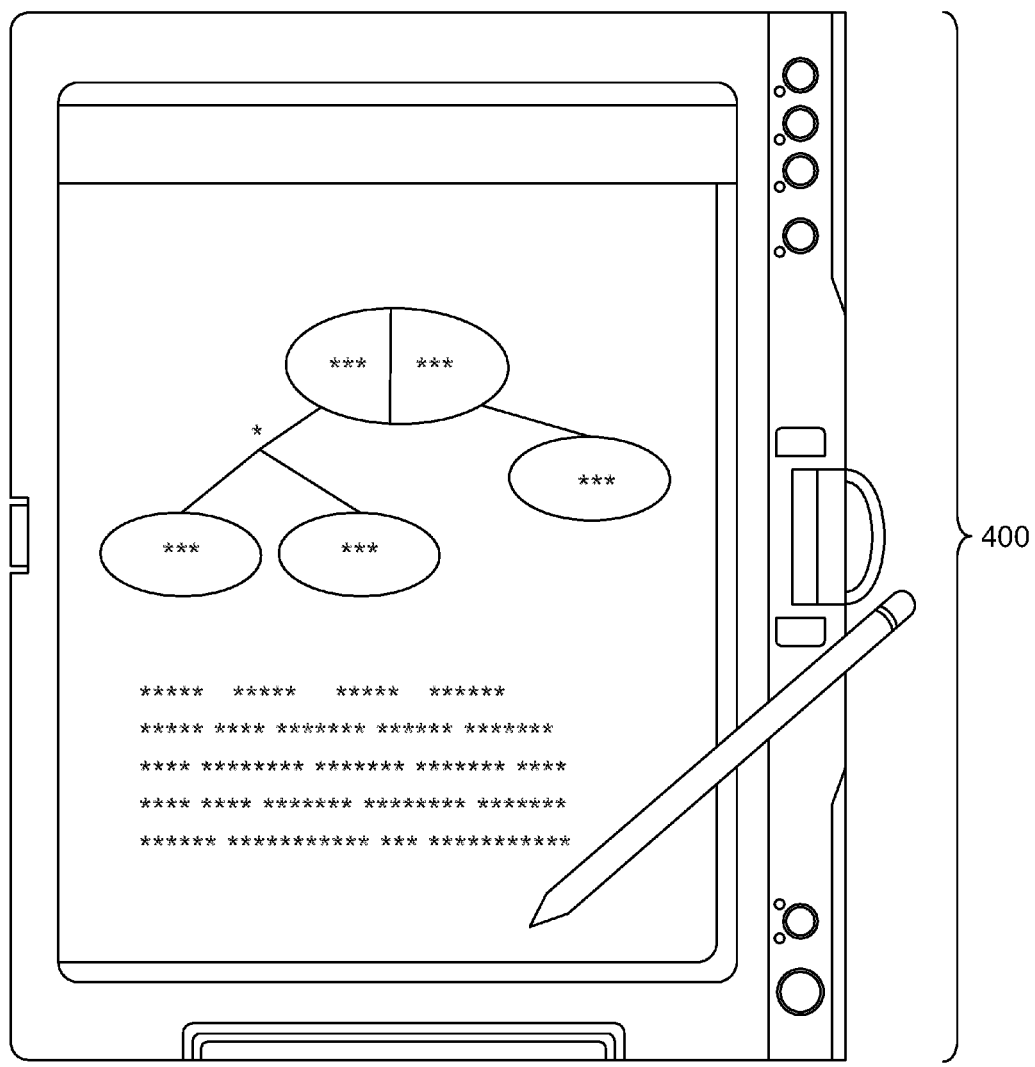
FIG. 4 is a graphical view illustrating a computing device called a tablet pc.
Figure 5:
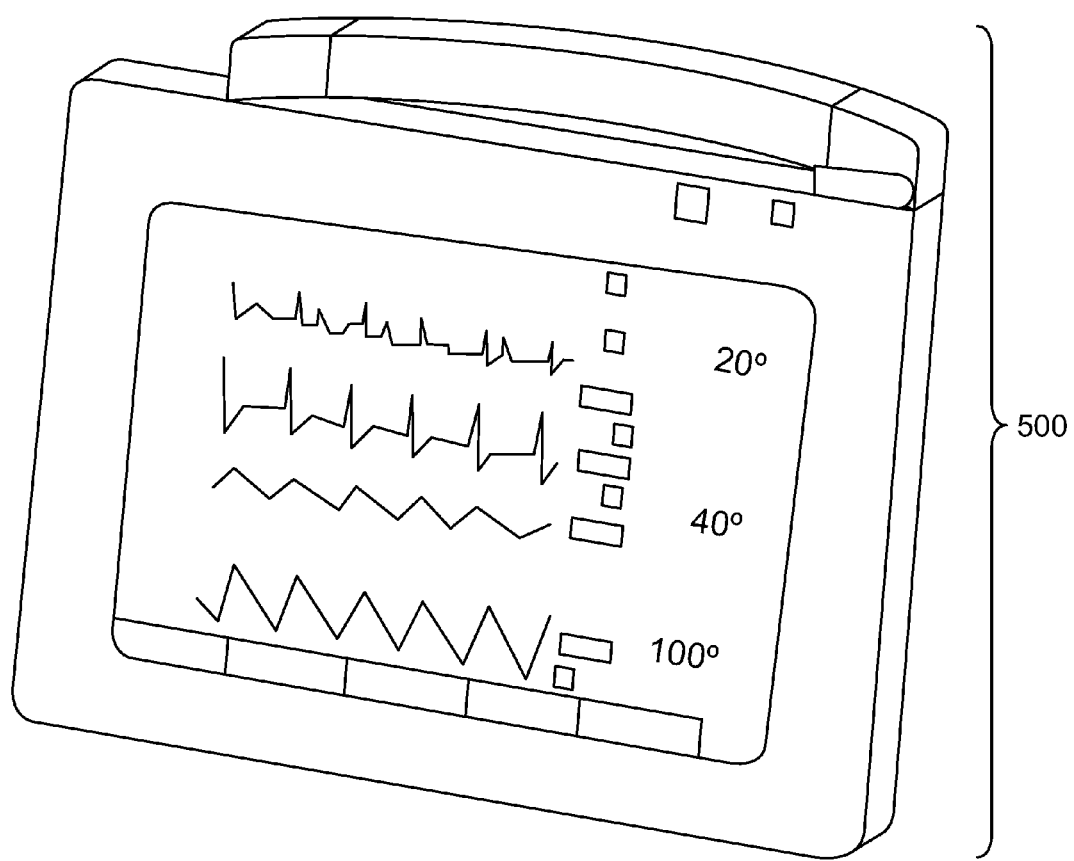
FIG. 5 is a graphical view illustrating a computing device called a portable device monitor.
Figure 6:
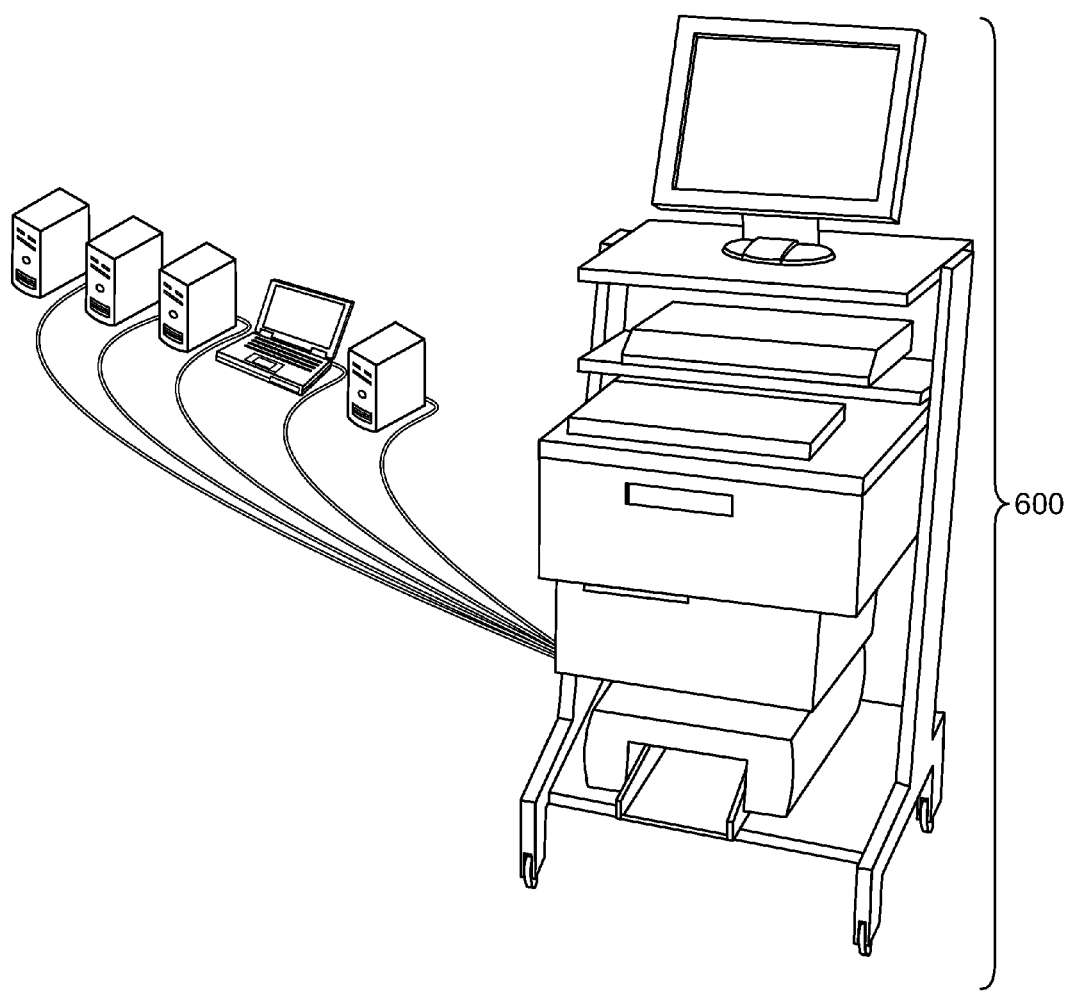
FIG. 6 is a graphical view illustrating a computing device called a data acquisition computing device.
Figure 7:
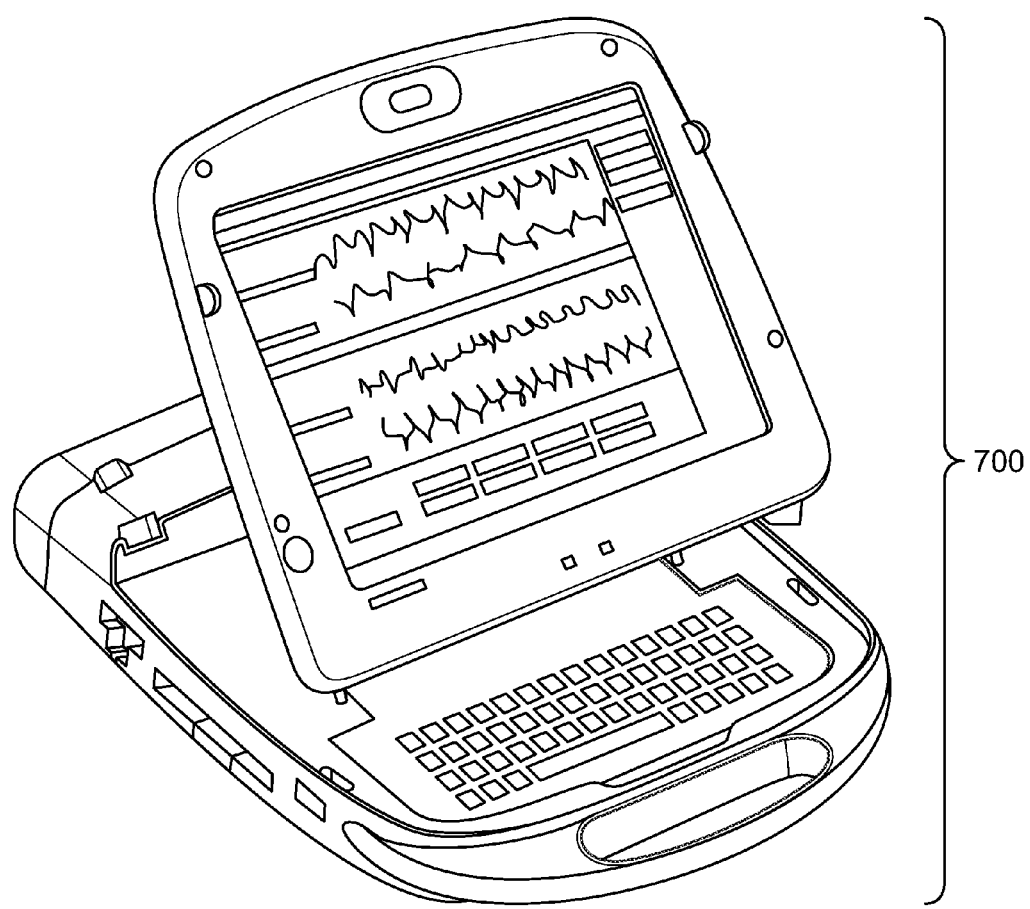
FIG. 7 is a graphical view illustrating a computing device called a stationary device monitor.
Figure 8:
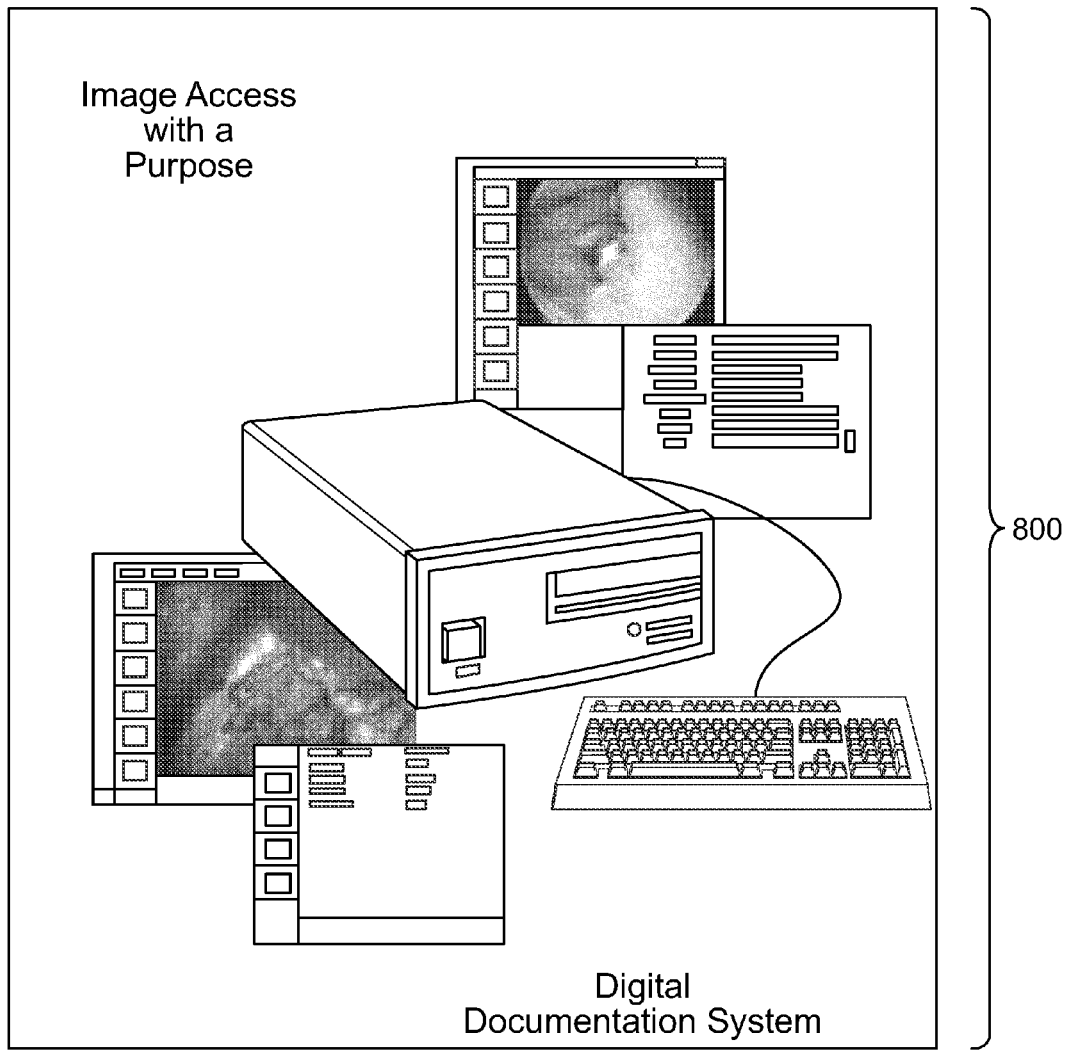
FIG. 8 is a graphical view illustrating a computing device called an image capture computing device.

Reference will now be made in detail to the present preferred embodiments of the present invention, examples of which are illustrated in the accompanying drawings, wherein like reference numerals refer to like elements throughout.

Figure 9:
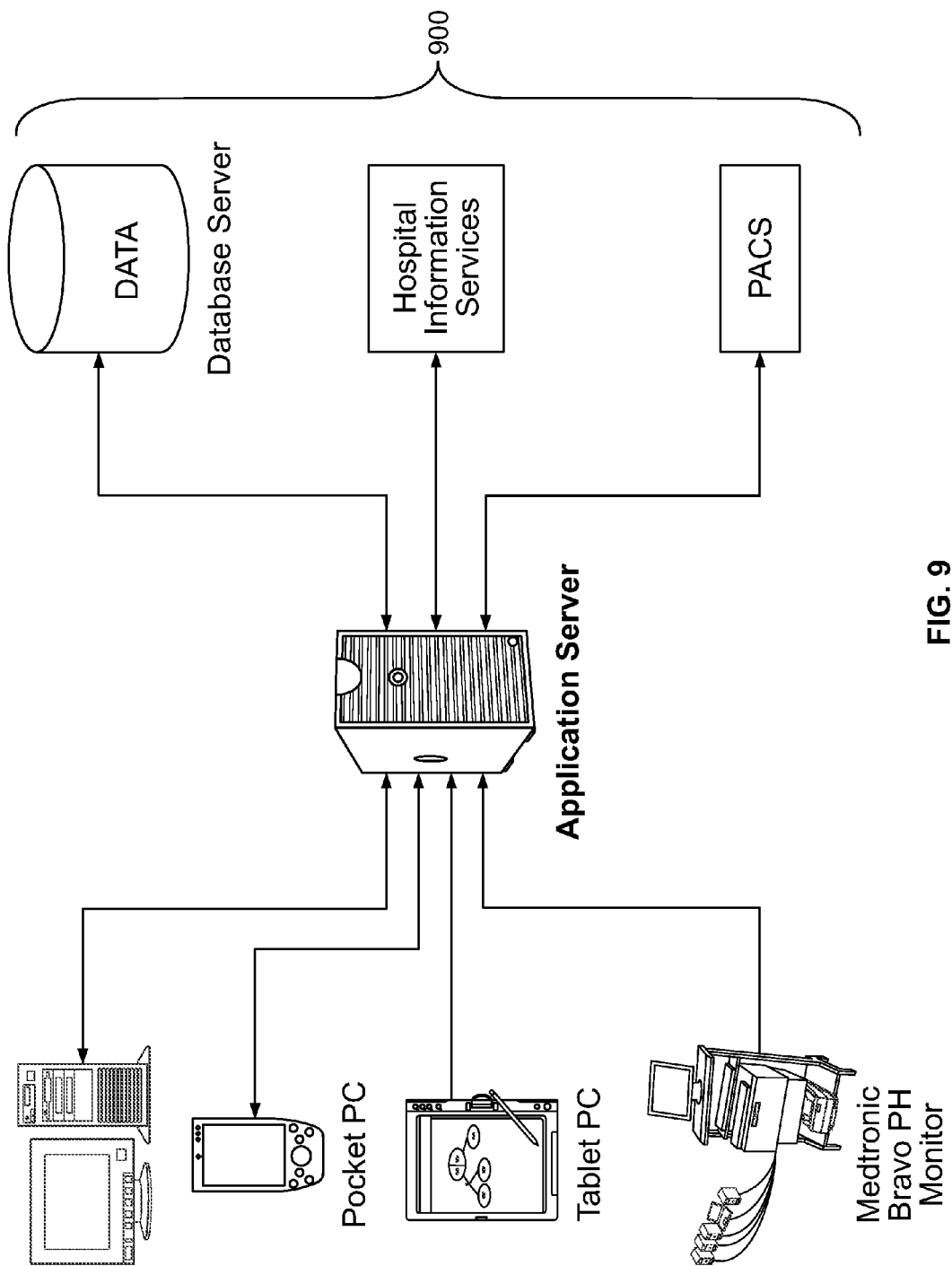
FIG. 9 is a graphical view illustrating a typical configuration of system architecture.
Figure 11:
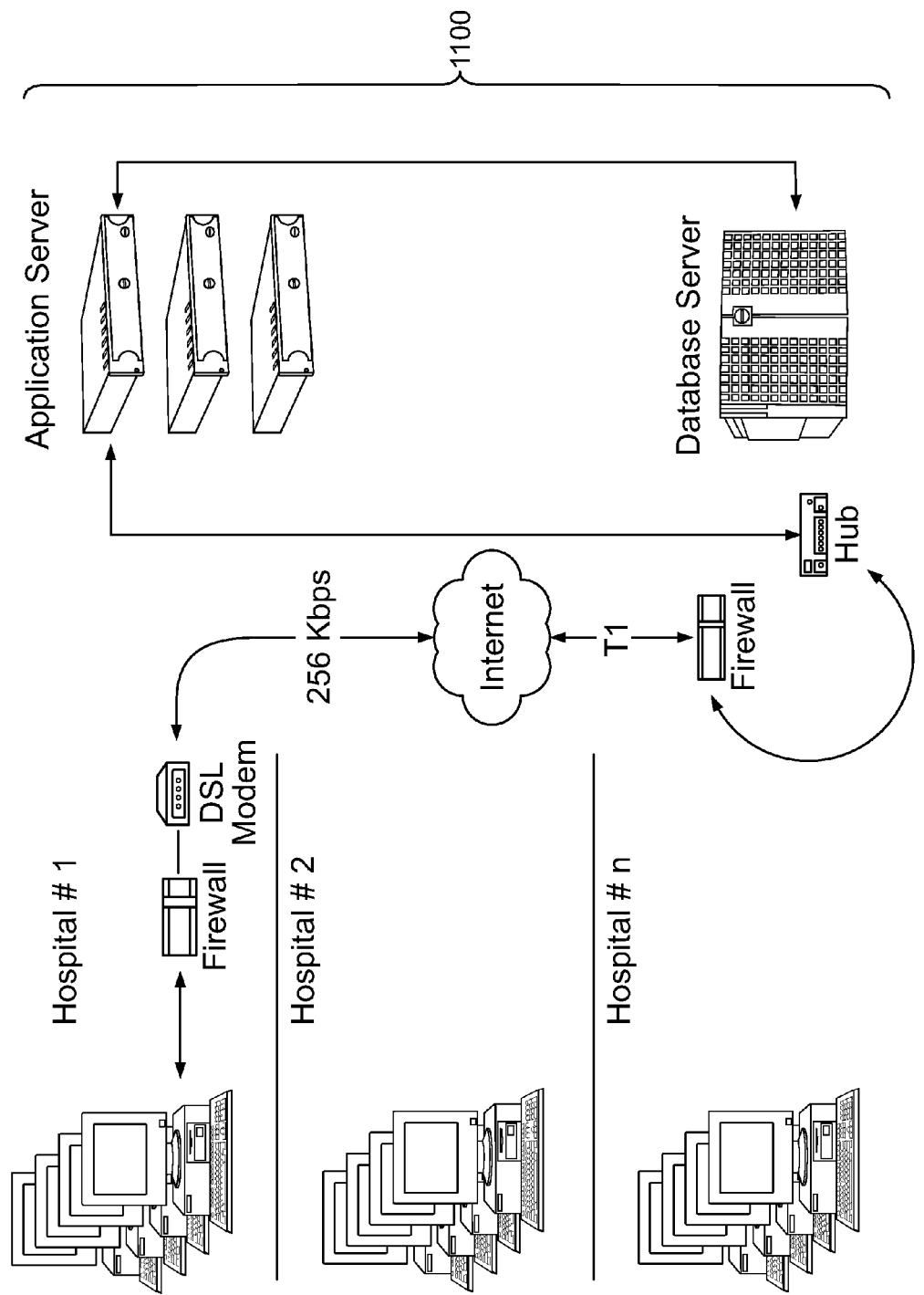
FIG. 11 is a graphical view illustrating the physical connections in a WAN and internet configuration of the system.

Referring to FIG. 9, the present invention includes a plurality of general purpose computing devices interconnected in networked configuration. Referring to FIG. 11, this networked configuration can be in the form of a LAN, WAN, ISDN, Internet, or wired or wireless networked configuration. Referring to FIG. 1 to FIG. 8, the general purpose computing devices can be any of a personal computing device 100, a laptop computing device 200, a Pocket PC 300, a tablet pc 400, a portable device monitor 500, a data capture computing device 600, a stationary device monitor 700, or an image capture device 800. The computing device can additionally or alternatively be any of the commonly known Windows/Intel PC, Apple Computers, Citrix ICA computers, Unix Workstations, and Linux workstations, and can be produced by vendors including but not limited to Sun, IBM, Compaq, Dell, Apple, and HP.

Figure 10:
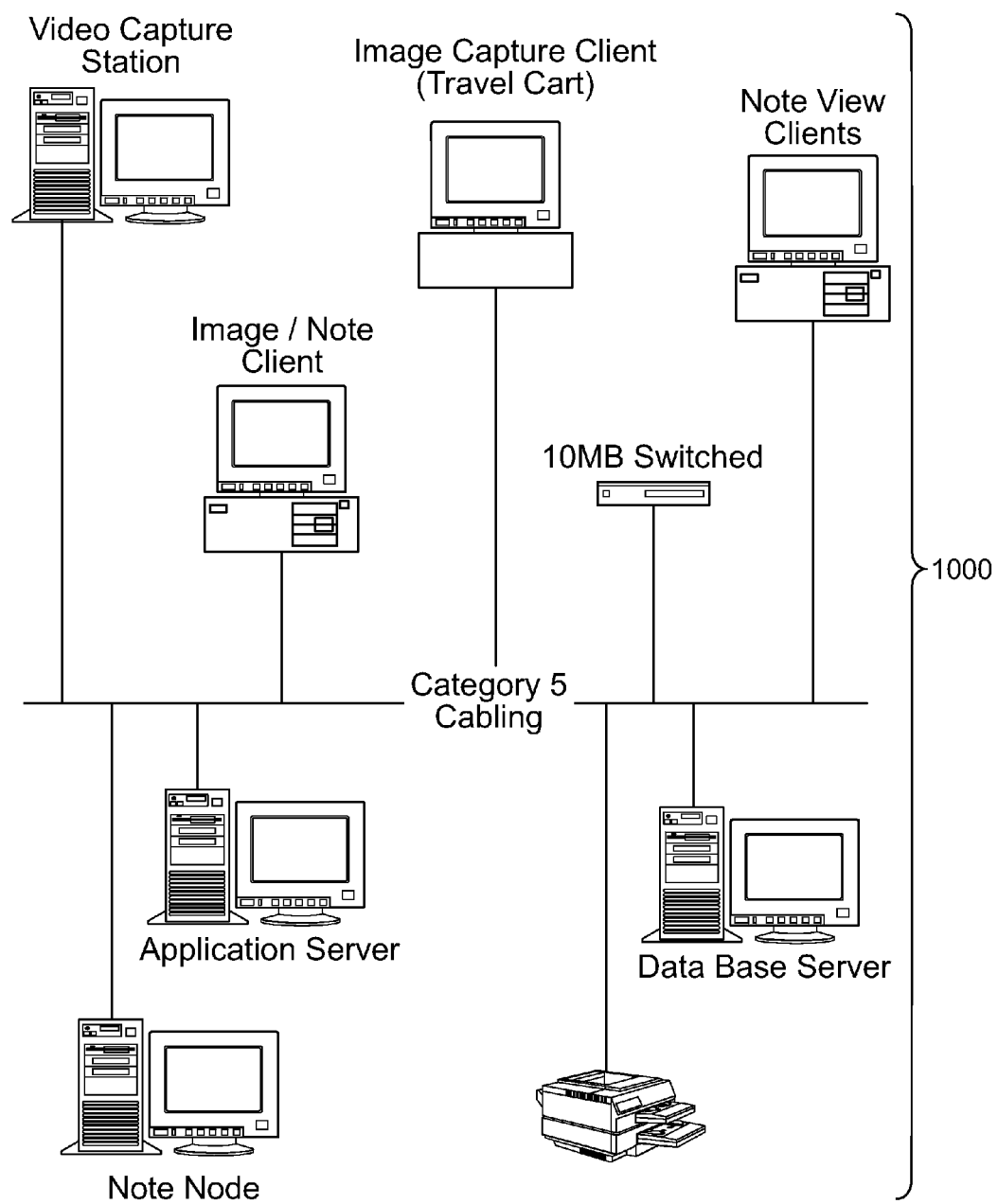
FIG. 10 is a graphical view illustrating the physical connections in a typical configuration of a system within the healthcare facility.

Referring to FIG. 10, the general purpose computing devices communicate with a database server via standard TPC/IP network wireless or wired protocols. The database, which includes a knowledge base in the form of a plurality of medical content specialties, is managed by the database server. The database can be any known database, such as relational, Object, text based, XML based, object-relational, and flat file, produced by vendors including but not limited to Oracle, Microsoft, Sybase, IBM, Computing device Associates, and Informix. The networked computing device system can be any of TPC/IP, Peer-to-Peer, Wireless, RPC, IPX/SPX, DLC, and Windows Networking, and can be produced by vendors including but not limited to IBM, Novell, Apple, RedHat, Unix, BSD, and Microsoft.

A plurality of printers is also included in this configuration. The computing devices may have their own local printers.

Figure 12:
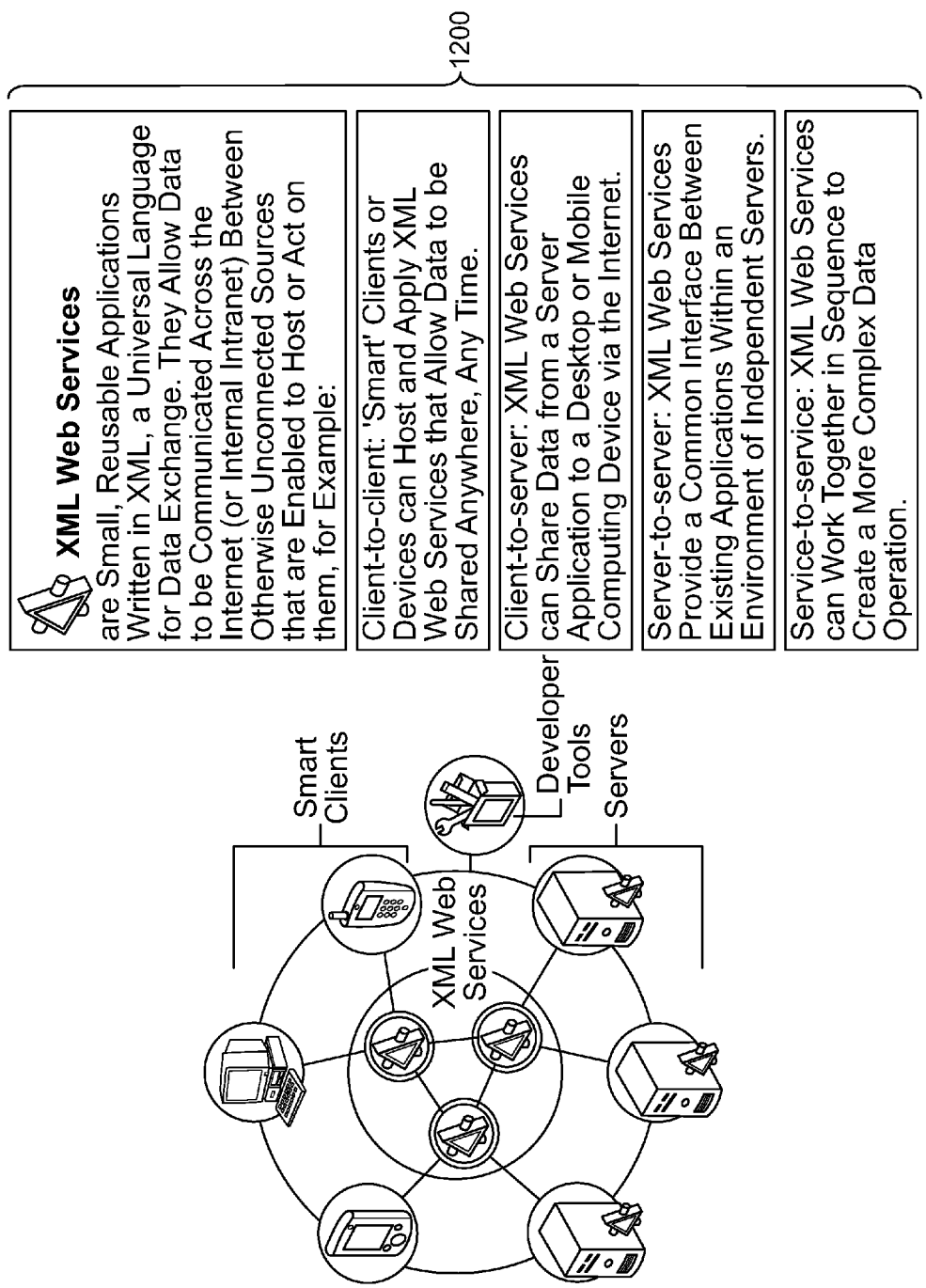
FIG. 12 is a graphical view illustrating the logical connections between the clients and servers.

The system is written with commercially available application development and database applications. The system can be written in any programming language using commercially available database system. Referring to FIG. 12, the current system runs on Windows computing devices but the present invention is not limited to any specific operating systems, programming language, database vendor, or computing device.

Figure 16:
FIG. 16 is a screen shot illustrating the anticipatory physician interface of system.

Referring to FIG. 16, a physician uses the invention by going through the anticipatory system menus to document the procedure or by using the diagramming method to document the procedure. The system is designed so that the physician is presented with natural procedure descriptors, in a manner that the physician would expect, and in a manner in which the physician would describe the procedure. Additionally, the system is designed so the physician can document his or her work in a diagramming method and that all of the necessary pieces of documentation are captured to ensure correct CPT and ICD9 coding.

To maximize the value of the information maintained by the system, it is important to facilitate both information entry, to ensure that the system can access all pertinent information, and information retrieval, to ensure that the information is accessible and that such retrieved information is accurately provided to the provider for proper interpretation. Further, the physicians must have confidence that the information is accurate, secure, and fail-safe; otherwise, physicians will be reluctant to rely upon the system for maintaining medical information.

In a typical configuration, the program modules of the system are organized in a multi-tier architecture. Several computing devices throughout the healthcare facility are equipped with the client-side components of the system, which can access other server-side components located on other computing devices via the network. The client-side system components physician user interface comprises a number of screens in a computing environment that prompts the physician for input and displaying output.

Examples of suitable user interfaces include traditional Windows clients, browser/HTML based, J2EE, JAVA, XML based, Windows Forms, Windows NET, Windows FX, speech recognition, speech navigation, and Pocket PC interfaces. These may be produced by vendors including but not limited to IBM, Novell, Apple, Sun, and Microsoft.

While the preferred implementation for a hospital setting is a network environment, many of the system functions, including the physician interface and data management functions can be performed on a single computing device.

The discussions are intended to provide a brief, general description of a suitable computing environment for the server and client computing devices. As noted previously, the system is implemented as a series of program modules, comprising computer executable instructions executed either on a server or client computing device. Generally, program modules include routines, programs, components, and data structures that perform specific coordinated and synchronized tasks.

Figure 13:
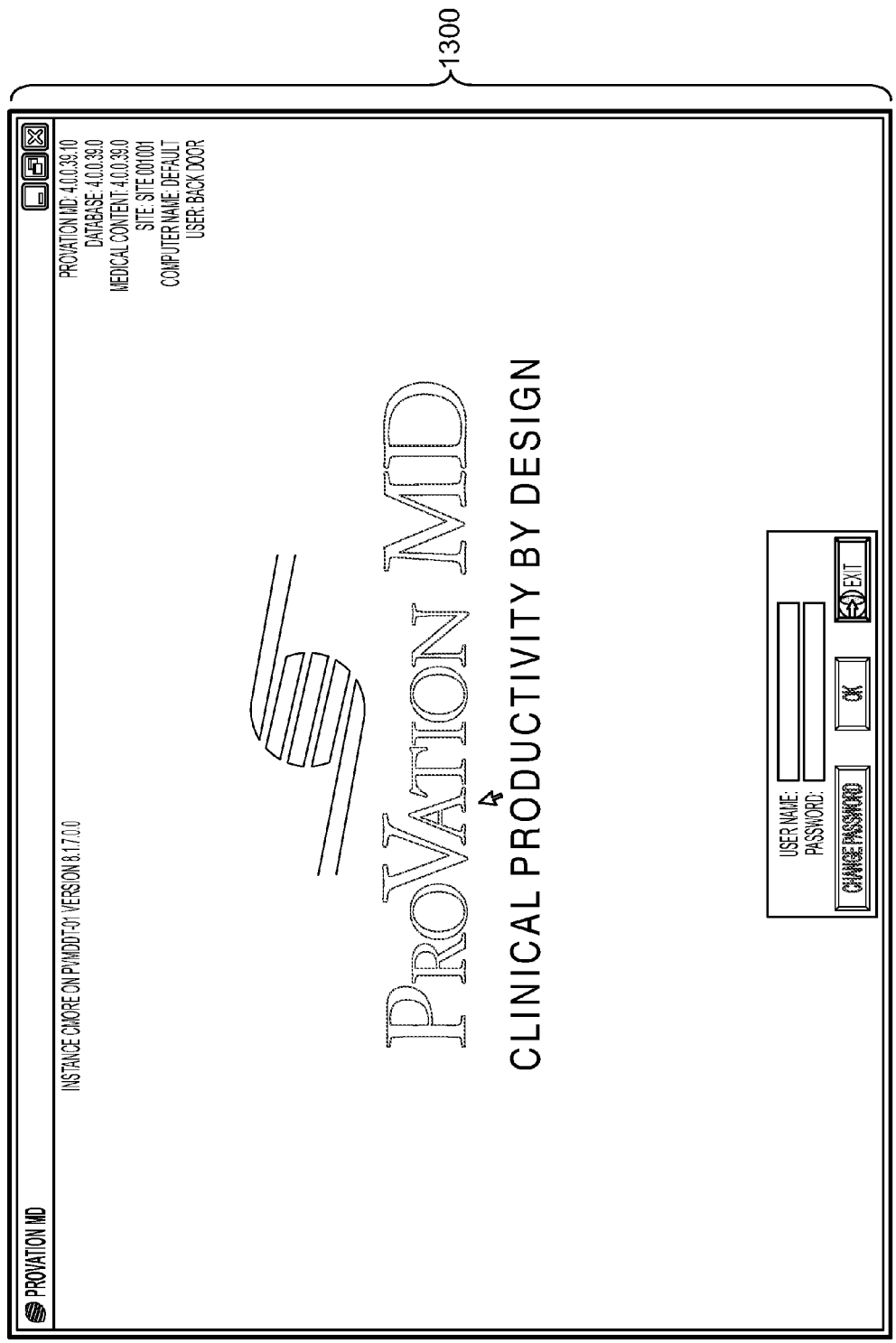
FIG. 13 is a screen shot illustrating the physician logon screen for the system.
Figure 14:
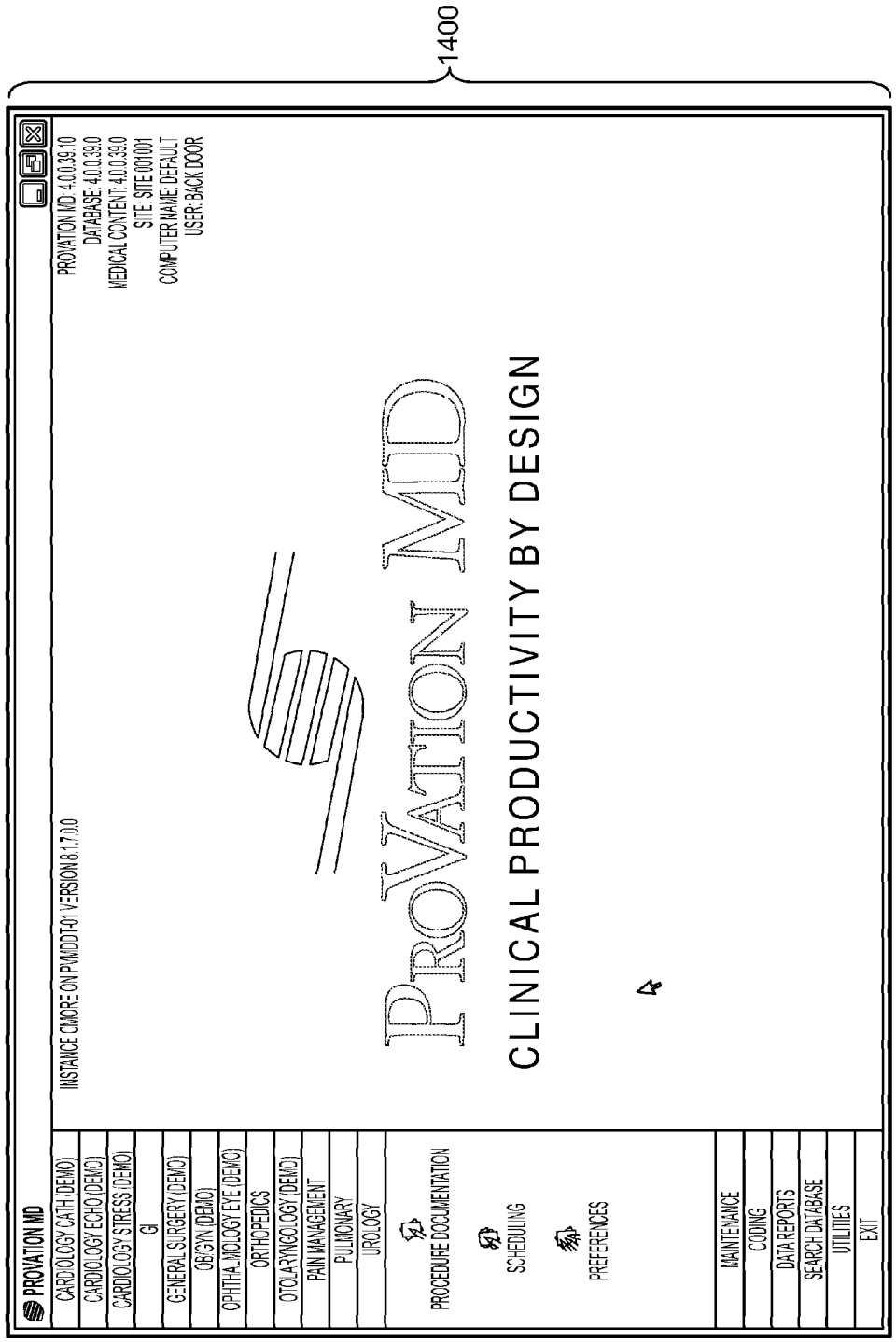
FIG. 14 is a screen shot illustrating the form that allows the physician to select the specialty for the procedure documentation.
Figure 15:
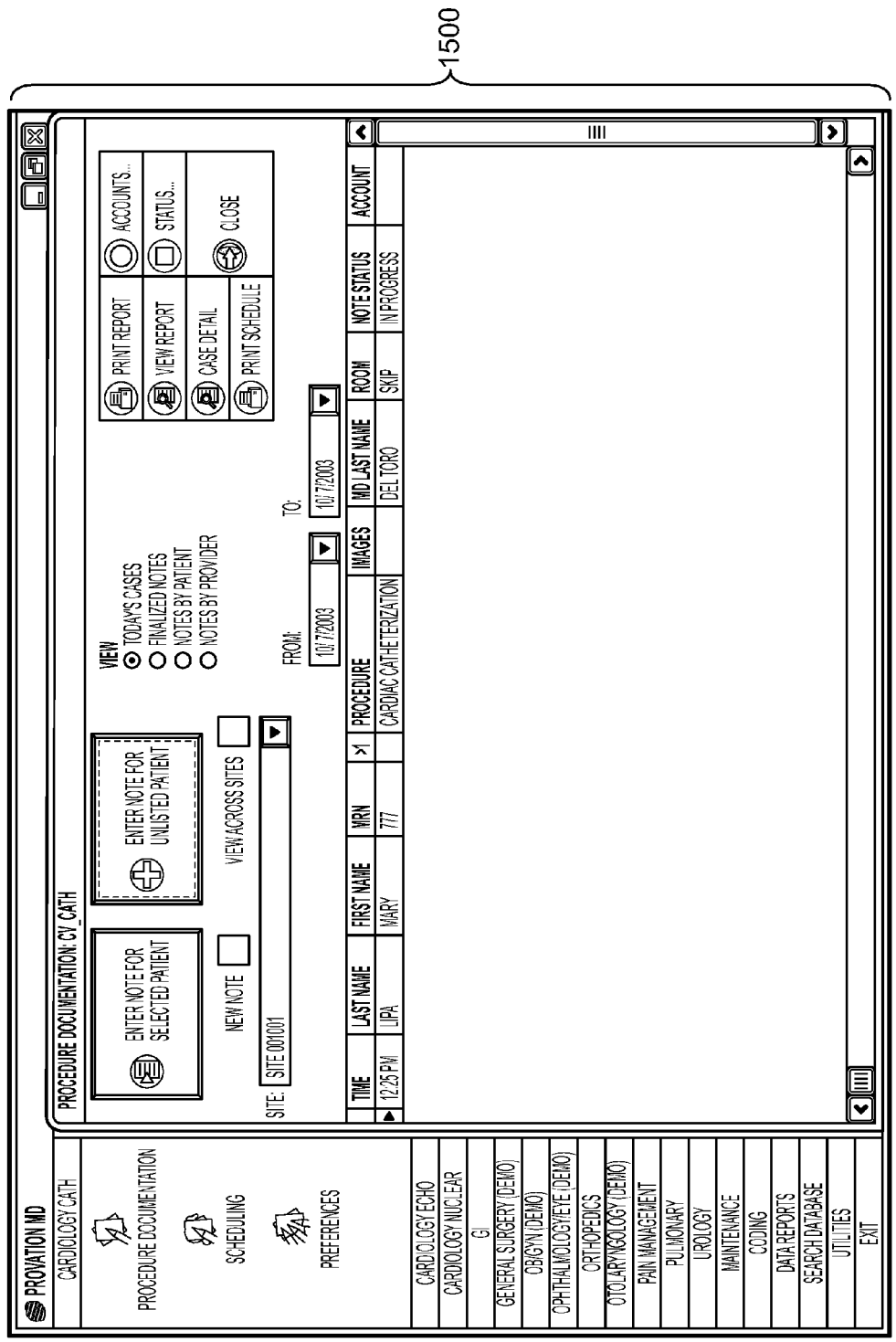
FIG. 15 is a screen shot illustrating the main selection form for the launching of the procedure documentation component.

The physician logs on to the system with a user name and password 1300 FIG. 13. After securing access to the system, referring now to FIG. 14, the physician is presented with a screen that allows them to select the specialty area for procedure documentation 1400. Referring now to FIG. 15, the physician is presented a listing of procedures that need procedure documentation 1500. The listings of procedures 1500 is typically generated by a scheduling interface or by scheduling personnel using the scheduling module 1700; see FIG. 17. The physician begins the documentation of the procedure by selecting rows of data in the listing of procedures 1500. The physician user interface then displays a screen illustrated in FIG. 18.

Figure 18:
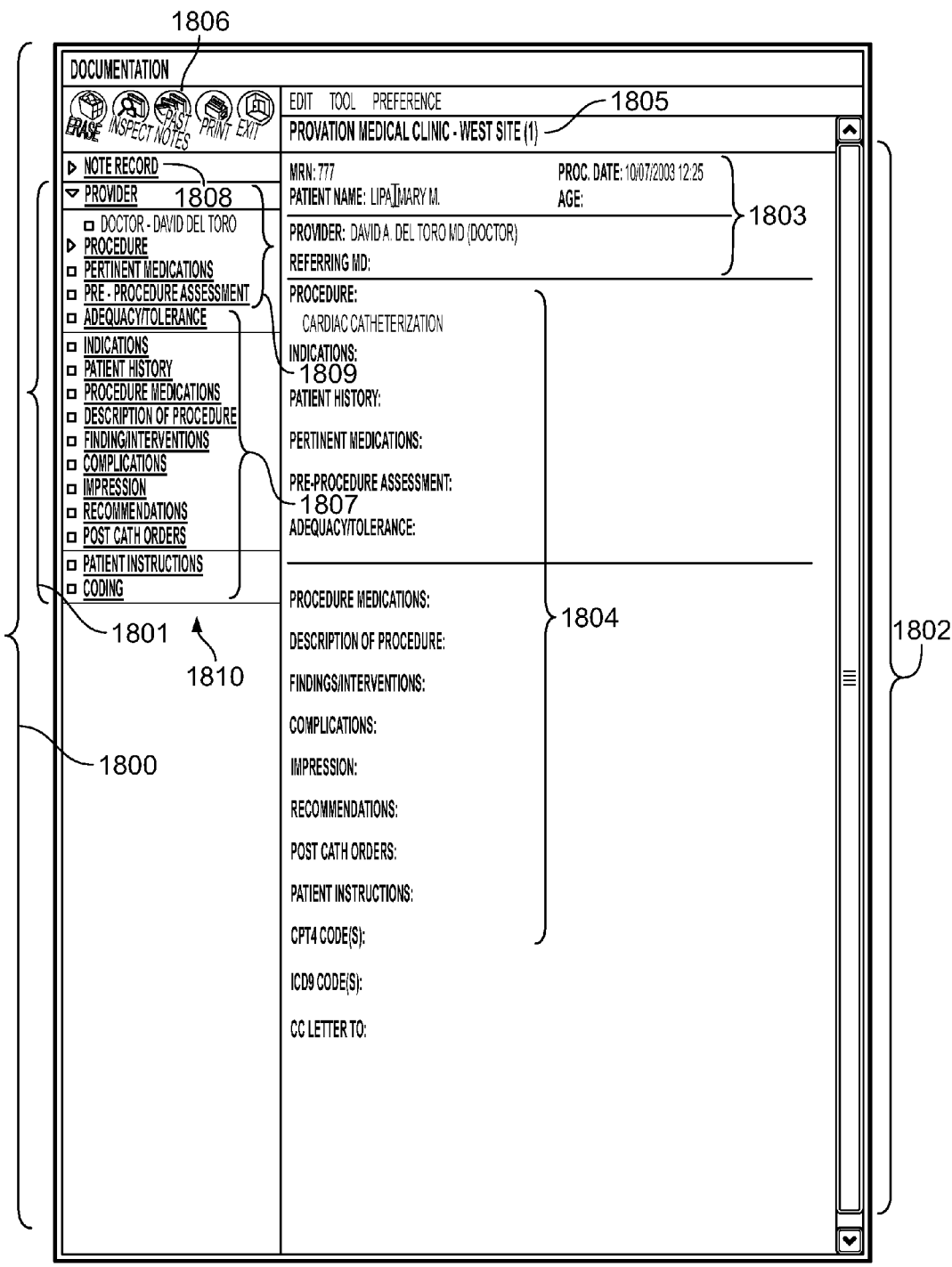
FIG. 18 is a screen shot illustrating the system's physician interface after selecting a patient that has undergone a procedure.

FIG. 18 is a screen shot illustrating the operation of a system program 1800, and more particularly the navigation tree and report area, according to an embodiment of the present invention. Referring now to FIG. 18, the display of the system program typically comprises a navigation tree 1801, a report area 1802, a program function icon area 1806, and a program function menu bar 1805. The system stores the data in a commercially available SQL database. The database is comprised of programming logic in the form of Structured Query Language SQL stored procedures and data tables.

Referring to FIG. 18, the navigation tree 1801 is comprised of several nodes 1809, 1807 that represent distinct areas of report documentation. One specific node, Note Record 1808 contains demographic information about the patient that is typically entered by the nursing or front desk personnel but can be automatically populated by an interface from the hospital information system. After entering data into the subnodes 1809 detailed within the Note Record 1808, the data is automatically copied to the demographic subsection 1803 of the report area 1802. Additional data is entered via the navigation tree 1801 by clicking on other nodes 1807. The data entered is automatically copied to subsection 1804 of the report area 1802.

The invention utilizes a well known and established object oriented design pattern documented in the book "Design Patterns—Elements of Reusable Object Oriented Software" by Gamma, Helm, Johnson, and Vlissides coupled with the invention's ontology inference engine that enables a documentation method utilizing a synchronized menu and diagramming system to generate the medical procedure descriptions.

The well-known object oriented design pattern is called the Observer Pattern in the book but is known by other names such as the Publish-Subscribe model. The key objects in the algorithm are the subject and observer. A subject may have any number of dependent observers. All observers are notified whenever the subject undergoes a change in state. In response, each observer will query the subject to synchronize its state with the subject's state. This kind of interaction is also known as publish-subscribe. The subject is the publisher of notifications. It sends out these notifications without having to know who its observers are. Any number of observers can subscribe to receive notifications.

Referring to the present invention, the system is managed by two primary subjects called Main Document and Diagram Document with a number of observers for each subject. Main Document and Diagram Document are programming object code that are responsible for keeping track of its observers and holding data before it is written to the database. The Main Document subject is responsible for the procedure note documentation functionality, see FIG. 19. The Diagram Document subject is responsible for the diagram documentation functionality, see FIG. 20.

Figure 20:
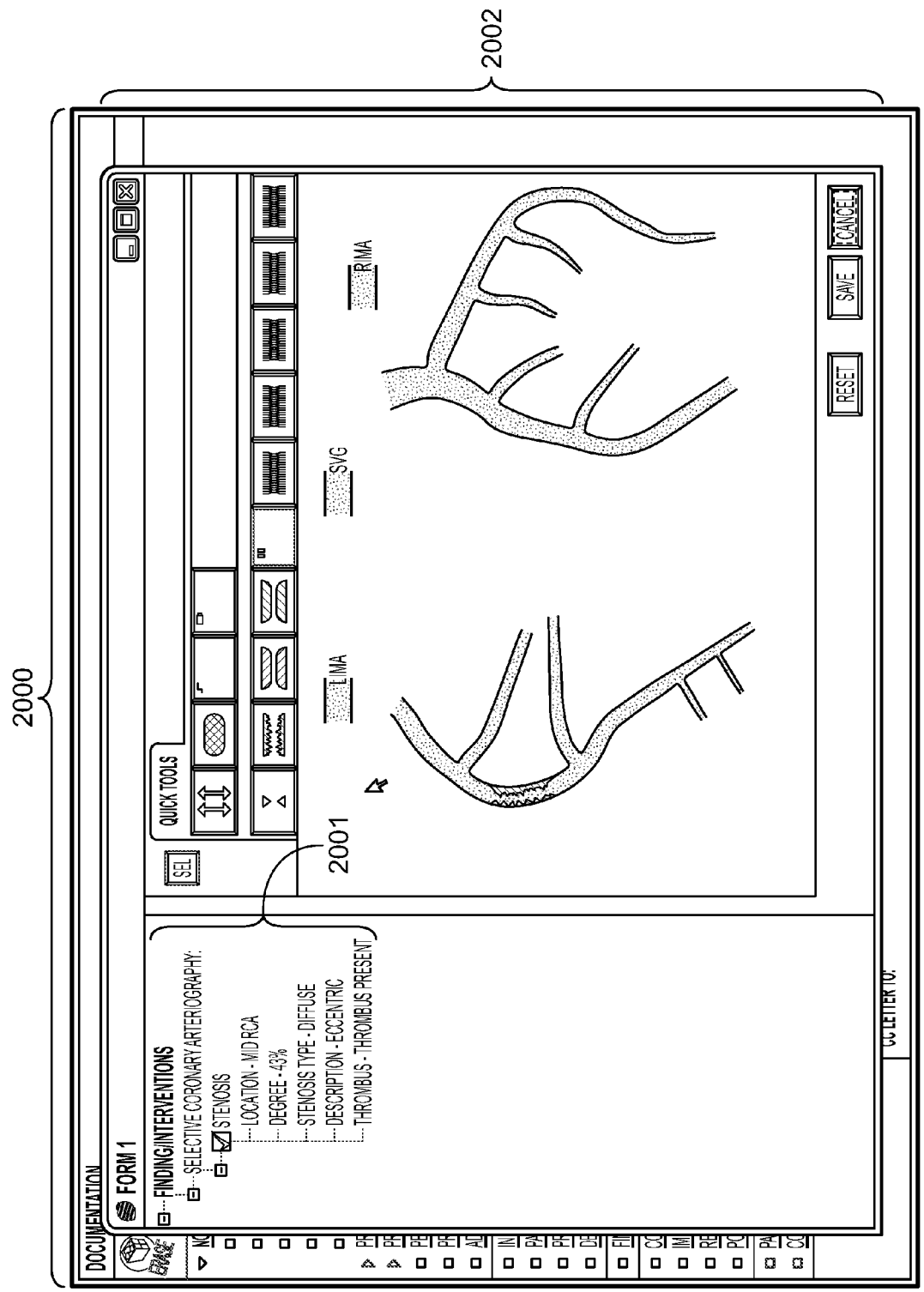
FIG. 20 is a screen shot illustrating the system's diagramming physician interface.

Referring to FIG. 19, the Main Document subject 1900 has two observers, Tree Menu 1901 and Edit Window 1902. Referring to FIG. 20, the Diagram Document subject 2000 has two observers, Diagram Tree Menu 2001 and Diagram Window 2002.

FIG. 21 is a screen shot illustrating the first step in the constructing of a procedure description. After the physician selects a patient record to document, the system creates a subject called Main Document and two observers called Tree Menu and Edit Window. The system informs the subject of its observers and the subject is now in control of the application. Main Document calls its observers, Tree Menu and Edit Window informing them that they need to get coordinated. After receiving this information from the subject, Main Document, the observers, Tree Menu and Edit Window, query the subject and retrieve the data that has changed.

Referring now to FIG. 21, the observers display the data which was retrieved 2100 from the Main Document subject. Main Document retrieved this data from the medical content database. The Tree Menu observer additionally has logic that auto-navigates the cursor to the most frequent procedure documented in the selected specialty 2101. Referring to FIG. 21, this is the menu selection Cardiac Cath 2101. In other medical specialties supported by the system, Tree Menu will automatically navigate to a node labeled Procedure Category. The physician also has the ability to navigate to the procedure node from any other node in the navigation tree.

The physician next selects their procedure from the menu 2100. The observer, Tree Menu, observes the menu selection and informs the subject, Main Document, of the data change. Main Document may be uncoordinated with its observer's Tree Menu and Edit Window and informs them that they need to get coordinated. The observers react to this message and then query the subject, Main Document, for the change in data and the screen is refreshed with the data selected, see FIG. 22. Tree Menu displays the menu selection 2201 underneath the procedure node and Edit Window displays the long name of the procedure 2200. The subject, Main Document, and the observers, Tree Menu and Edit Window, are now synchronized.

Figure 23:
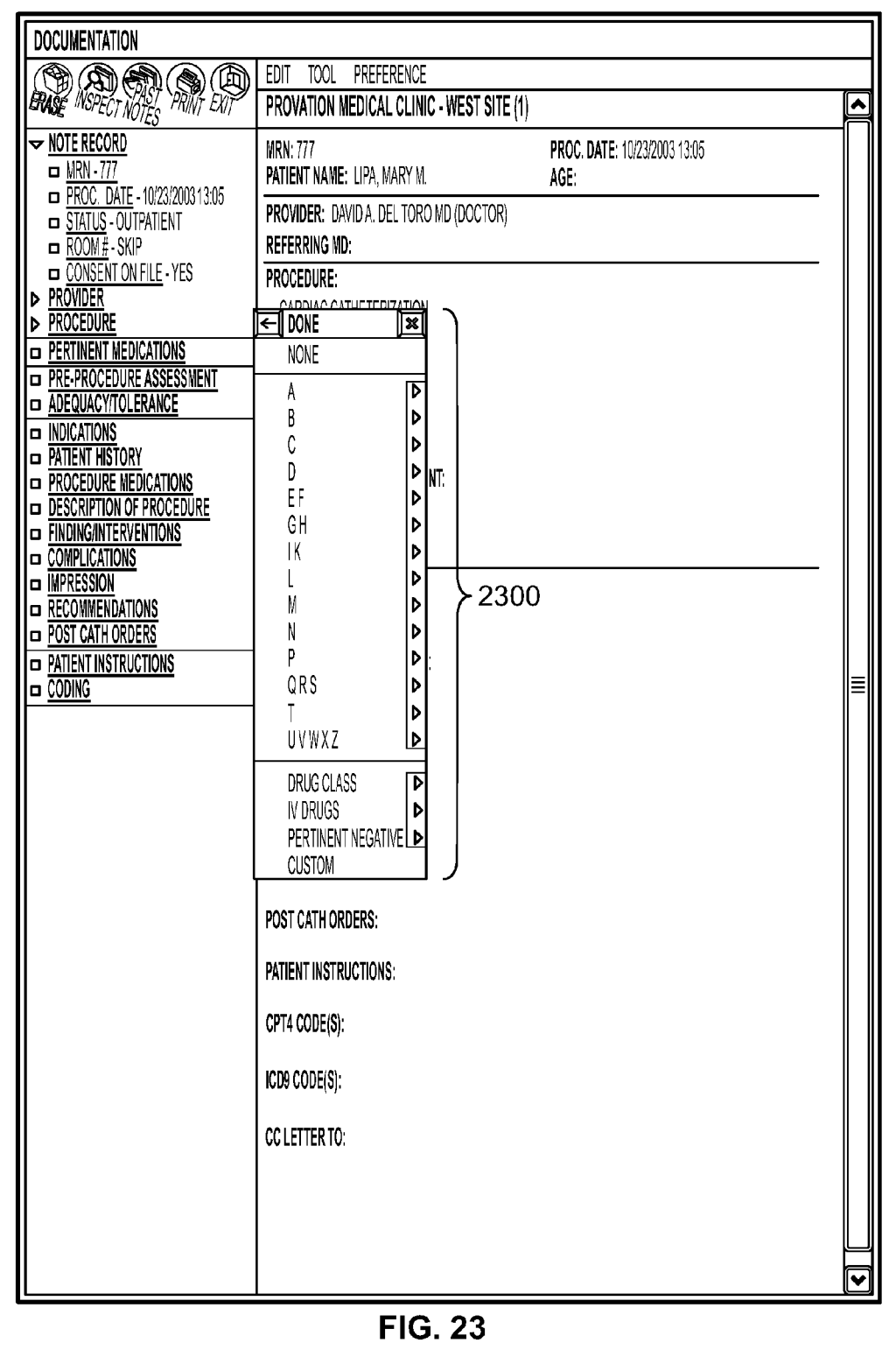

Referring now to FIG. 23, the physician is next presented with a pertinent medications menu 2300. The same interactions described above between the subject, Main Document and the observers, Tree Menu and Edit Window, occur each time a menu is presented and selected by the physician. The physician makes the menu selection. The observer, Tree Menu, observes the menu selection and informs the subject, Main Document, of the data change. Main Document may be uncoordinated with its observer's Tree Menu and Edit Window and informs them that they need to get coordinated. The observers react to this message and then query the subject, Main Document, for the change in data and the screen is refreshed with the data selected. Tree Menu displays the menu selection underneath the corresponding node and Edit Window displays the text associated with the menu selections. The subject, Main Document, and the observers, Tree Menu and Edit Windows, are now synchronized.

The physician could continue to document their procedure note using the aforementioned method. Alternatively, the physician could choose to document the procedure using the diagramming approach, see FIG. 20. The diagram approach utilizes a subject called Diagram Document and two observers called Diagram Tree Menu and Diagram Window. Referring to FIG. 24, the diagram method of procedure documentation can be activated any number of ways and in this example, the activation is initiated via a menu selection called Diagram Documentation 2400.

After the physician selects the menu selection, Diagram Documentation 2400, the system creates a subject called Diagram Document and two observers called Diagram Tree Menu and Diagram Window. The system informs the subject of its observers and the subject is now in control of the application. Diagram Document calls its observers, Diagram Tree Menu and Diagram Window informing them that they need to get coordinated. After receiving this information from the subject the observers, Diagram Tree Menu and Diagram Window query the subject and retrieve the data that has changed.

The data retrieved by the observers is processed by the ontology inference engine. The ontology inference engine maps the data elements between the menu data elements and diagram data elements. This mapping enables the synchronization between the two disparate representations of data.

Figure 25:
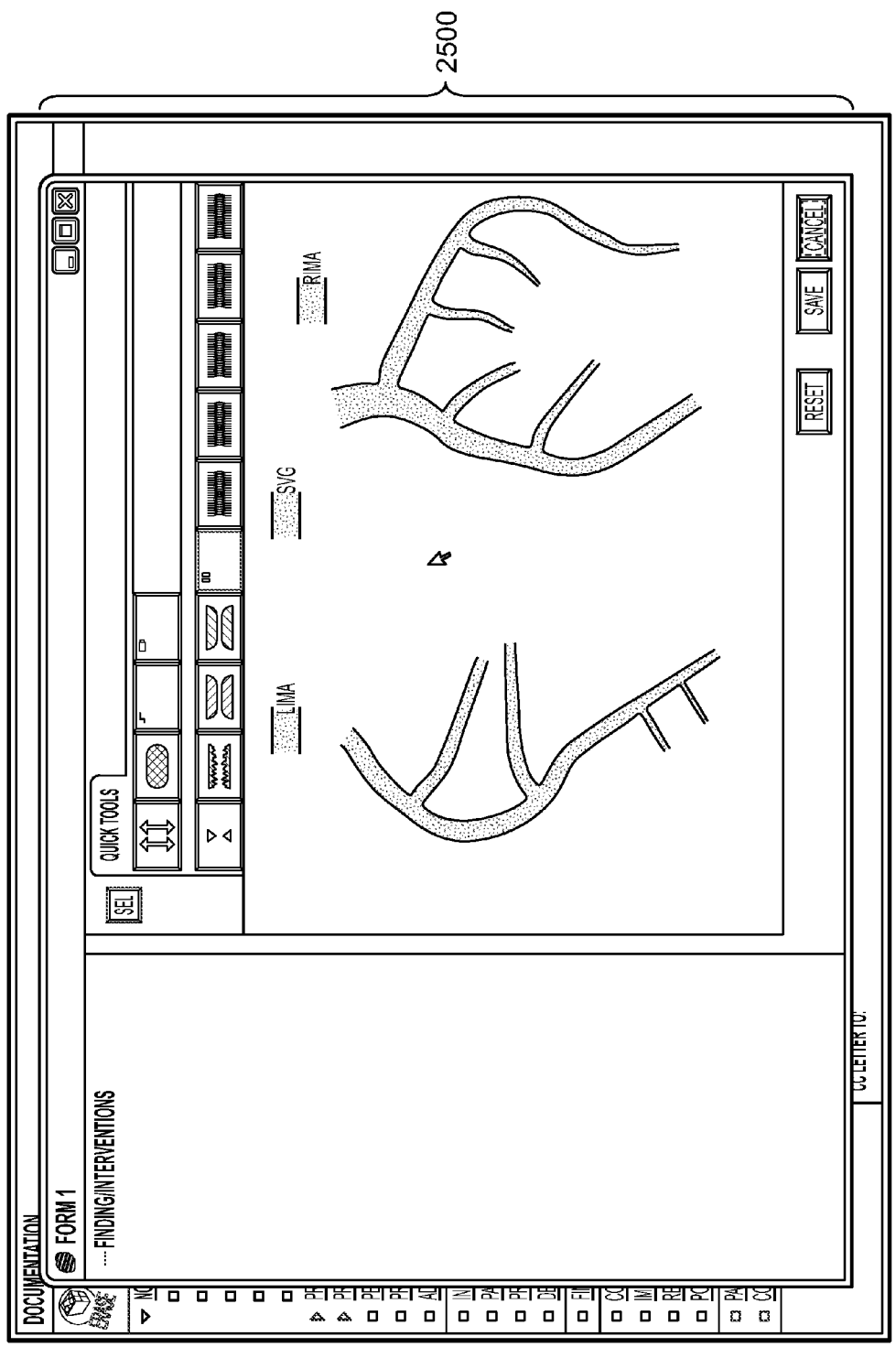
FIG. 25 is a screen shot illustrating the system's diagramming physician interface.

Referring now to FIG. 25, the observers, Diagram Tree Menu and Diagram Window, display the data 2500 which was retrieved from the Diagram Document subject. Diagram Document retrieved this data from the medical content database and the information associated with the selected patient. The diagram displayed was a diagram that was linked to a specific set of procedures. In this example, nothing has been previously documented therefore the diagram that is shown is the default diagram. The subject, Diagram Document, and its observers, Diagram Tree Menu and Diagram Window, are now synchronized.

Figure 26:
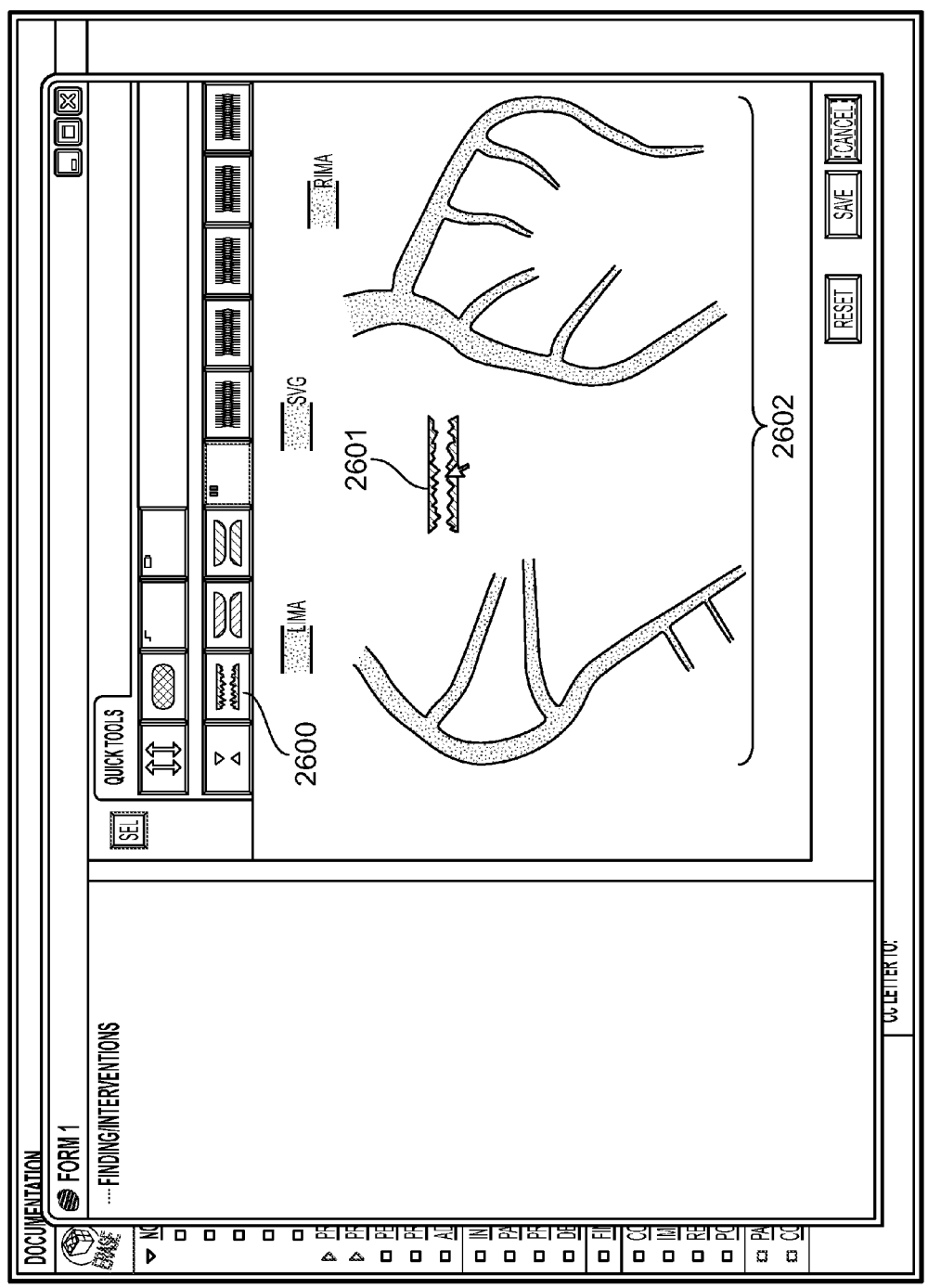
FIG. 26 is a screen shot illustrating the system's diagramming physician interface after a stenosis has been selected.

The physician, in this example, decides to document a stenosis in an artery. Referring now to FIG. 26, the physician clicks on the icon 2600 associated with a diffuse stenosis. The Diagram Window observer responses to the click and presents the physician with an enhanced cursor that looks like a diffuse stenosis 2601. The physician has full control to move the enhanced cursor and can place it within any artery 2602. The subject, Diagram Document, has not been notified of any changes and the observer, Diagram Window, is in control.

Figure 27:
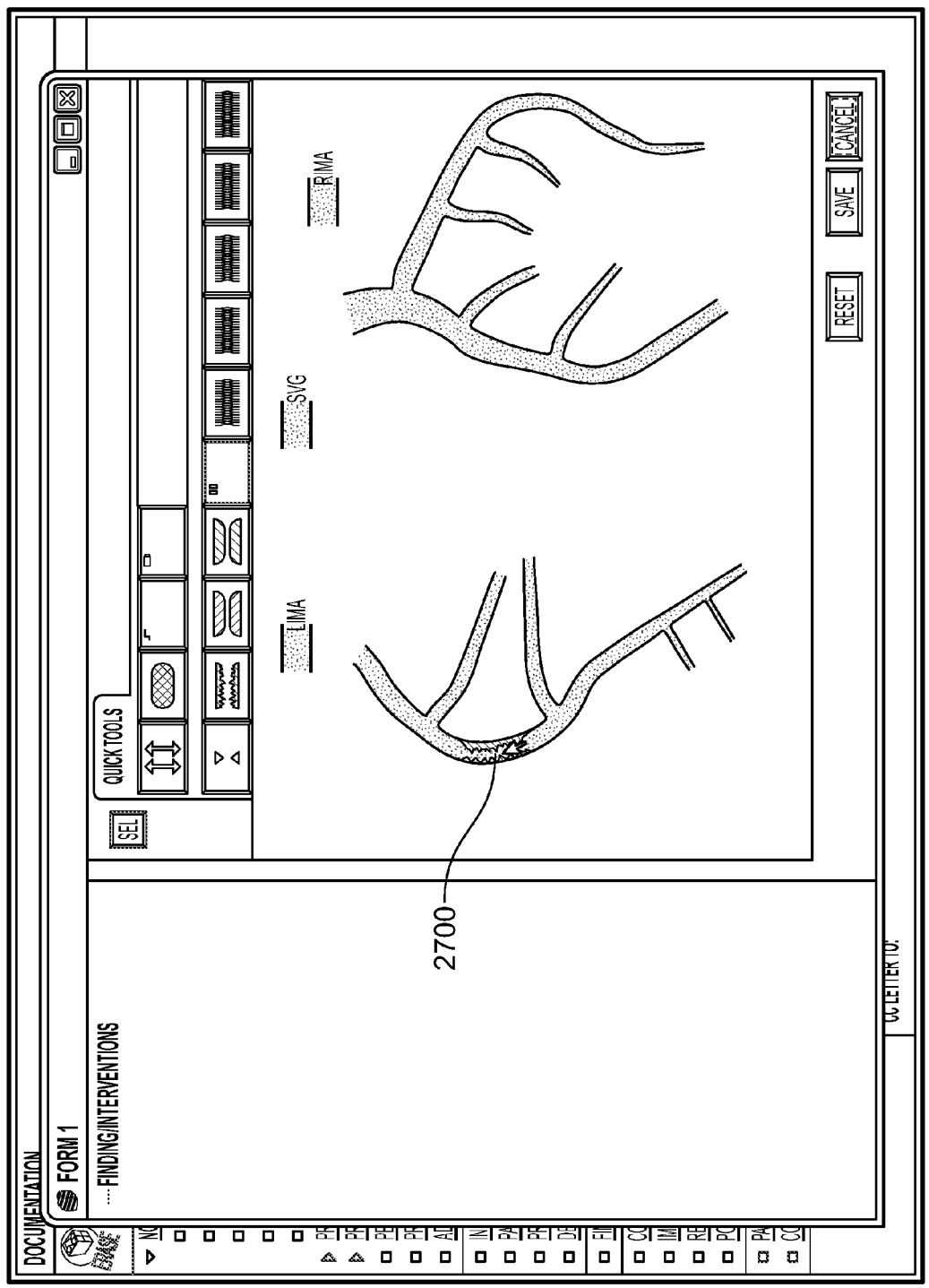
FIG. 27 is a screen shot illustrating the system's diagramming physician interface after a stenosis has been placed in an artery.

Referring now to FIG. 27, the physician has determined that the location of the diffuse stenosis was in the mid-right coronary artery and moves the enhanced cursor to a location on the diagram and places the stenosis in this location 2700 by clicking on the mouse button. The Diagram Window observer responds to this action and notifies it subject, Diagram Document, of the change in state. Diagram Document may be uncoordinated with its observer's Diagram Tree Menu and Diagram Window and informs them that they need to get coordinated. Diagram Document calls its observers, Diagram Tree Menu and Diagram Window informing them that they need to get coordinated. After receiving this information from the subject the observers, Diagram Tree Menu and Diagram Window query the subject and retrieve the data that has changed.

The data retrieved by the observers is processed by the ontology inference engine. The ontology inference engine maps the data elements between the menu data elements and diagram data elements. This mapping enables the synchronization between the two disparate representations of data.

Figure 28:
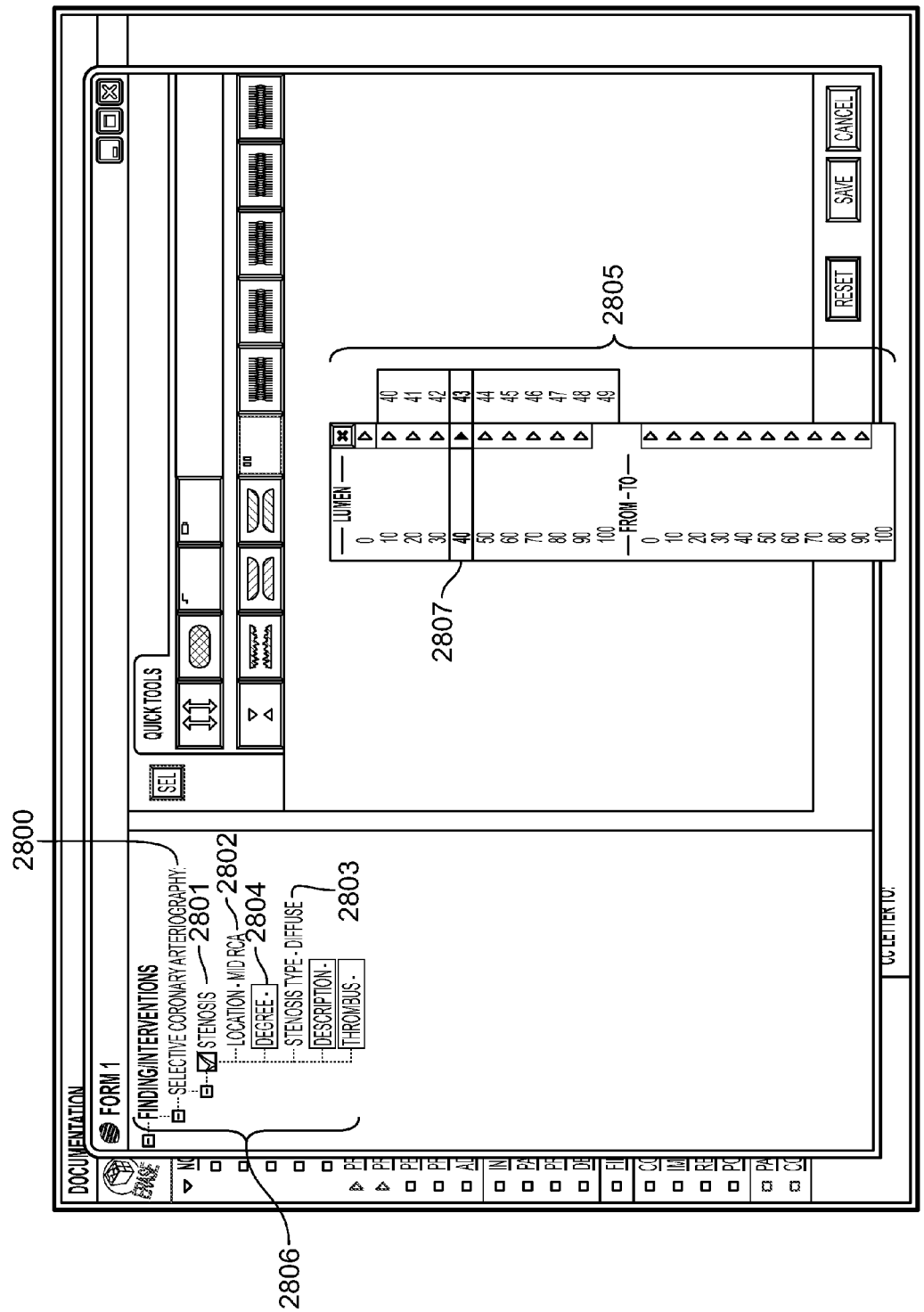
FIG. 28 is a screen shot illustrating the system's diagramming physician interface requiring additional data entry for the procedure.

Referring now to FIG. 28, Diagram Tree Menu observer displays data that is the result of the diffuse stenosis being placed in a specific location, see FIG. 27. A selective Coronary Arteriography 2800 with a stenosis 2801 is displayed in the tree 2806, with the location of Mid RCA 2802, and stenosis type of Diffuse 2803. The Diagram Window observer calls the subject, Diagram Document, and refreshes its data set and receives information from the subject that additional actions are required. The subject, Diagram Document, and the observers, Diagram Tree Menu and Diagram Window, are now synchronized.

The Diagram Windows observer reacts to the additional actions given to it by the Diagram Document subject. Referring to FIG. 28, the additional actions present the physician with menu selections necessary to complete the findings for the stenosis 2805. The physician needs to document the degree 2804 of the lumen 2805 for the stenosis 2801 and in this example; the physician selects 43 degrees 2807. The Diagram Window observer responds to this action and notifies it subject, Diagram Document, of the change in state. Diagram Document may be uncoordinated with its observer's Diagram Tree Menu and Diagram Window and informs them that they need to get coordinated. Diagram Document calls its observers, Diagram Tree Menu and Diagram Window informing them that they need to get coordinated. After receiving this information from the subject the observers, Diagram Tree Menu and Diagram Window query the subject and retrieve the data that has changed.

The data retrieved by the observers is processed by the ontology inference engine. The ontology inference engine maps the data elements between the menu data elements and diagram data elements. This mapping enables the synchronization between the two disparate representations of data.

Figure 29:
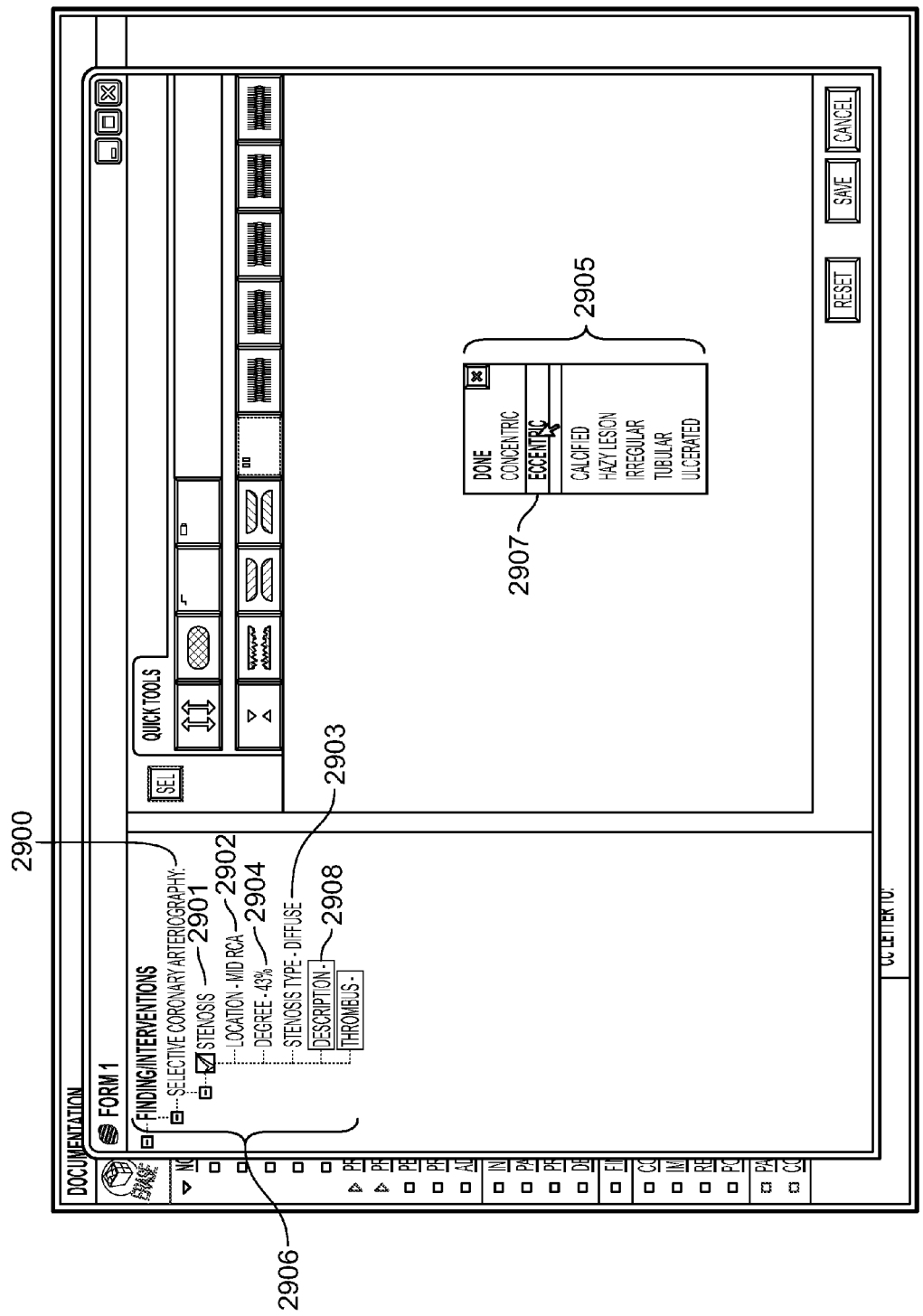
FIG. 29 is a screen shot illustrating the system's diagramming physician interface requiring additional data entry for the procedure.

The Diagram Tree Menu observer displays data 2904 that is the result of the degree selection, see FIG. 29. The Diagram Window observer calls the subject Diagram Document, refreshes its data set, and receives information from the subject that additional actions are required. The diagram is updated accordingly by selections that affect the structure of the diagram. The subject, Diagram Document, and the observers, Diagram Tree Menu and Diagram Window, are now synchronized.

The Diagram Windows observer reacts to the additional actions given to it by the Diagram Document subject. Referring to FIG. 29, the additional actions present the physician with menu selections necessary to complete the findings for the stenosis 2905. The physician needs to document the description 2908 for the stenosis 2901 and in this example; the physician selects Eccentric 2907. The Diagram Window observer responds to this action and notifies it subject, Diagram Document, of the change in state. Diagram Document may be uncoordinated with its observer's Diagram Tree Menu and Diagram Window and informs them that they need to get coordinated. Diagram Document calls its observers, Diagram Tree Menu and Diagram Window informing them that they need to get coordinated. After receiving this information from the subject the observers, Diagram Tree Menu and Diagram Window query the subject and retrieve the data that has changed.

The data retrieved by the observers is processed by the ontology inference engine. The ontology inference engine maps the data elements between the menu data elements and diagram data elements. This mapping enables the synchronization between the two disparate representations of data.

Figure 30:
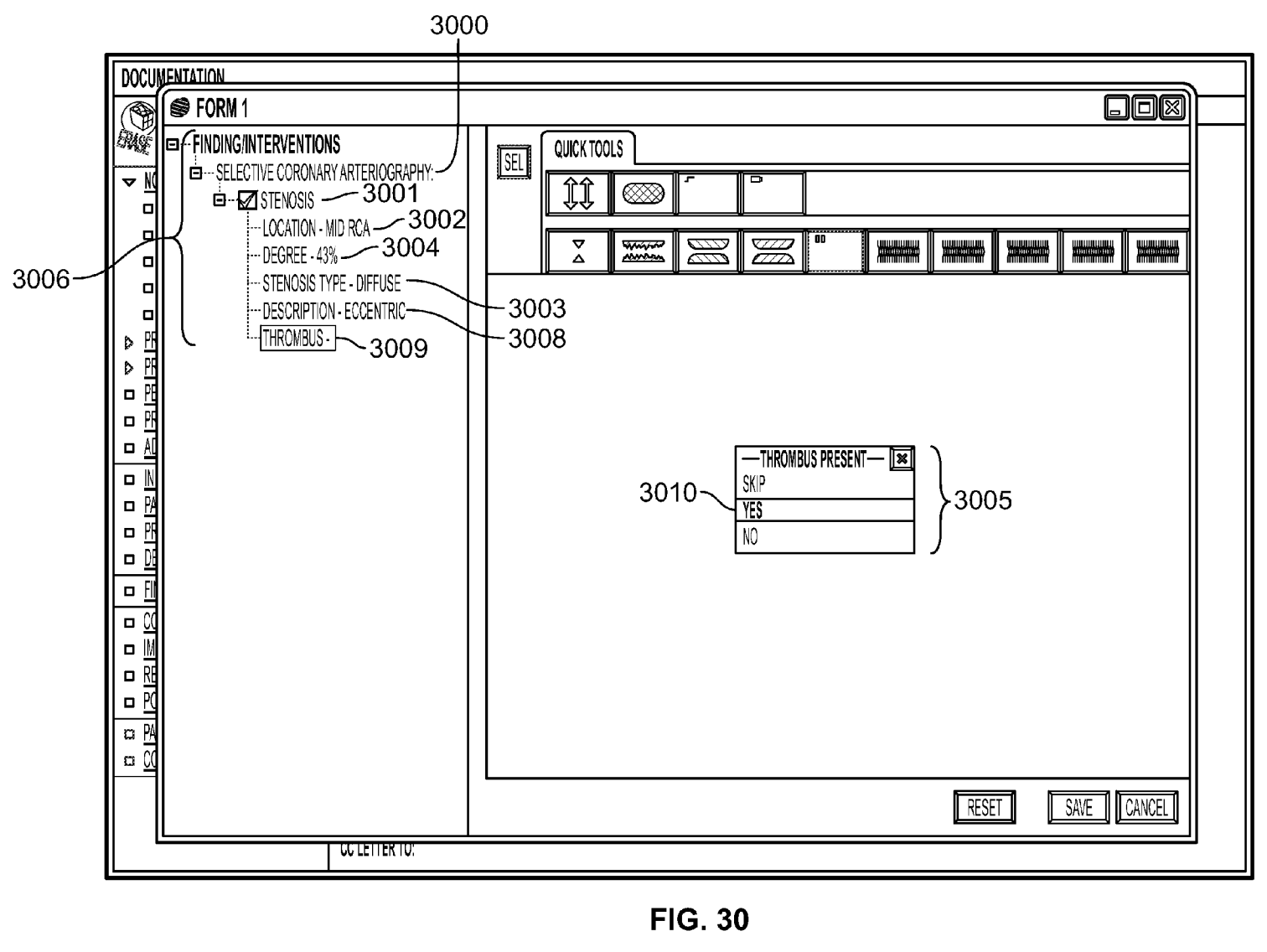

The Diagram Tree Menu observer displays data 3008 that is the result of the description selection, see FIG. 30. The diagram is updated accordingly by selections that affect the structure of the diagram. The Diagram Window observer calls the subject, Diagram Document, refreshes its data set, and receives information from the subject that additional actions are required. The subject, Diagram Document, and the observers, Diagram Tree Menu and Diagram Window, are now synchronized.

The Diagram Windows observer reacts to the additional actions given to it by the Diagram Document subject. Referring to FIG. 30, the additional actions present the physician with menu selections necessary to complete the findings for the stenosis 3005. The physician needs to document the Thrombus 3009 for the stenosis 3001 and in this example; the physician selects YES 3010. The Diagram Window observer responds to this action and notifies it subject, Diagram Document, of the change in state. Diagram Document may be uncoordinated with its observer's, Diagram Tree Menu and Diagram Window, and informs them that they need to get coordinated. Diagram Document calls its observers, Diagram Tree Menu and Diagram Window informing them that they need to get coordinated. After receiving this information from the subject the observers, Diagram Tree Menu and Diagram Window query the subject and retrieve the data that has changed.

The data retrieved by the observers is processed by the ontology inference engine. The ontology inference engine maps the data elements between the menu data elements and diagram data elements. This mapping enables the synchronization between the two disparate representations of data.

Figure 31:
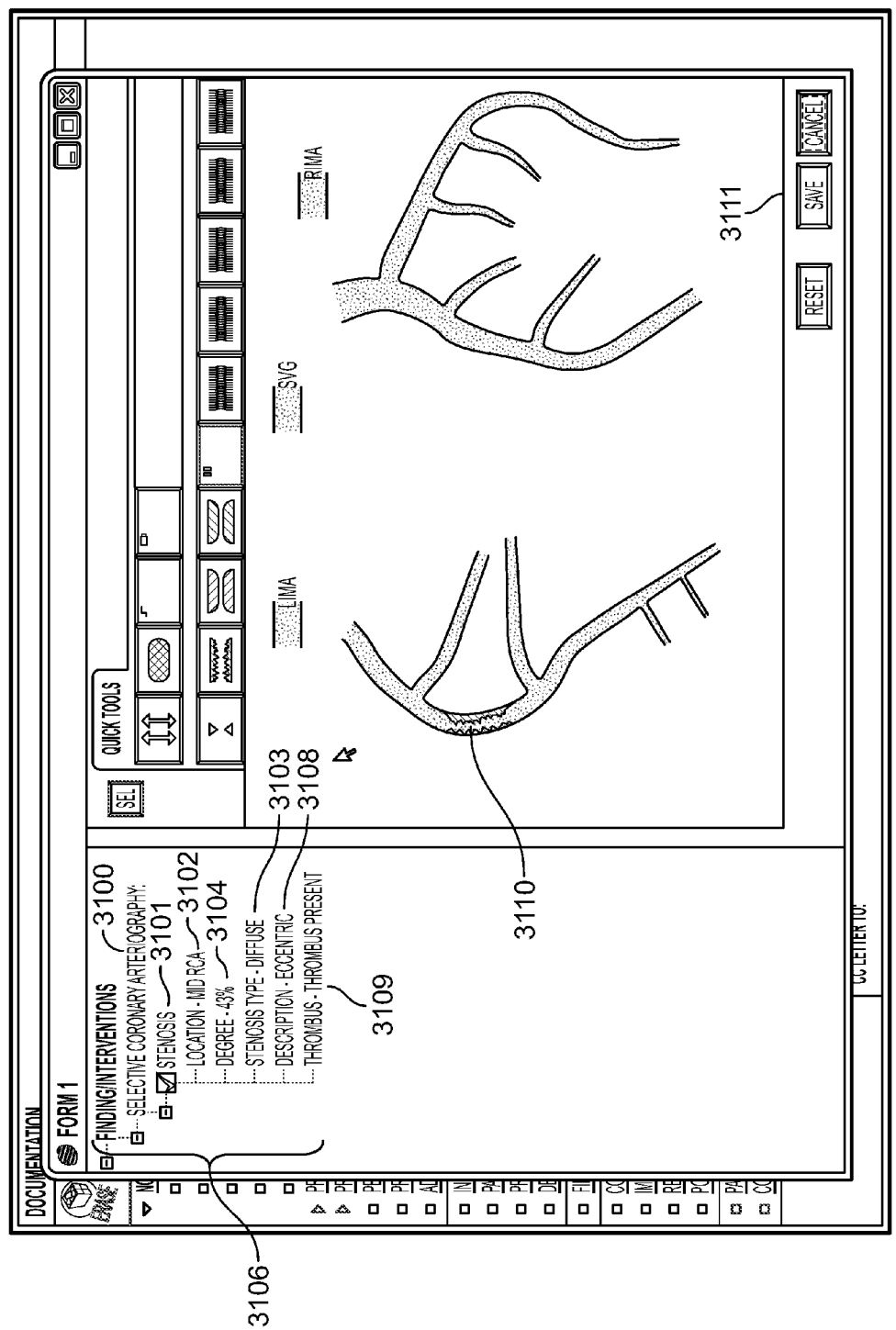
FIG. 31 is a screen shot illustrating the system's diagramming physician interface after all data entry is completed and before physician selects the save button.

The Diagram Tree Menu observer displays data 3109 that is the result of the Thrombus selection, see FIG. 31. The diagram is updated accordingly by selections that affect the structure of the diagram. The Diagram Window observer calls the subject, Diagram Document, refreshes its data set, and receives information from the subject that no additional actions are required. The subject, Diagram Document, and the observers, Diagram Tree Menu and Diagram Window, are now synchronized and the physician is presented with FIG. 31. In this example, the physician is satisfied with their documentation and hits the Save key 3111. The subject, Diagram Document, writes all of its data to the database and program control is now returned to the Main Document subject and its observers Tree Menu and Edit Window.

The system creates a subject called Main Document and two observers called Tree Menu and Edit Window. The system informs the subject of its observers and the subject is now in control of the application. Main Document calls its observers, Tree Menu and Edit Window informing them that they need to get coordinated. After receiving this information from the subject the observers, Tree Menu and Edit Window query the subject and retrieve the data that has changed.

Referring now to FIG. 32, the observer Tree Menu displays the data 3200 which was retrieved from the Main Document subject. The observer, Edit Windows, displays the data 3201 which was retrieved from the Main Document subject. Main Document retrieved this data from the medical content database and the patient database.

A system for the generating of naturally expressed medical procedure descriptions via a synchronized diagram and menu system has been described when documenting via the diagramming functionality. The procedure description documented in the diagram where propagated and synchronized with the menus. Now we need to describe the synchronized diagram and menu system when documenting via the menu functionality.

Figure 34:
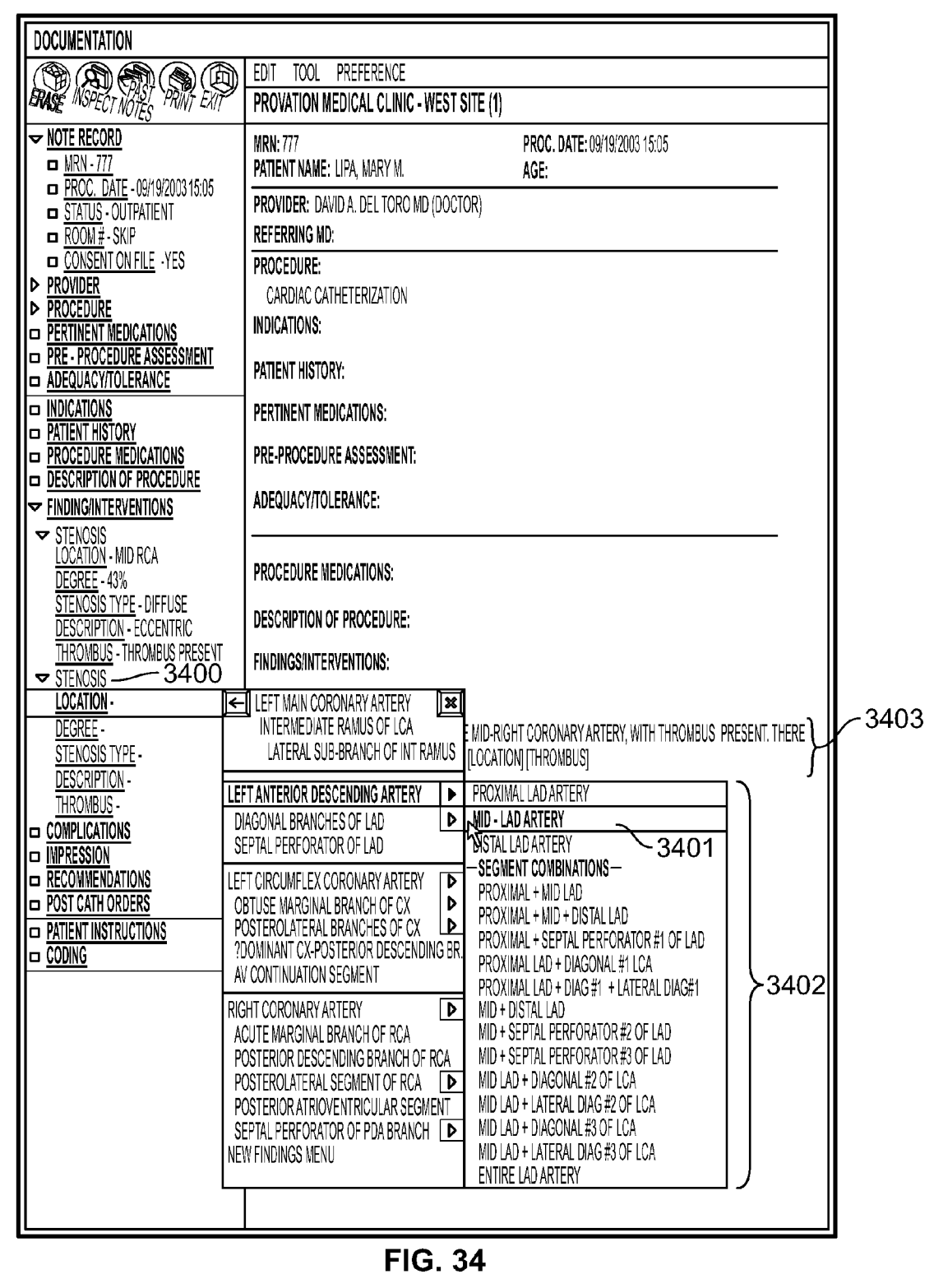

Now referring to FIG. 33, the physician navigates to the findings tree node 3301 and is presented with the menu tree 3302 and in this example, the finding information 3304 documented during the diagram documentation described previously. In the next example, the physician will be documenting a stenosis found in a different artery via the menu tree. The physician selects the menu selection Stenosis 3303. The observer, Tree Menu, observes the menu selection and informs the subject, Main Document, of the data change. Main Document may be uncoordinated with its observer's Tree Menu and Edit Window and informs them that they need to get coordinated. The observers react to this message and then query the subject, Main Document, for the change in data and the screen is refreshed with the data selected Referring to FIG. 34, the observer, Edit Window, displays the text string associated with a stenosis 3403 and the observer, Tree Menu, displays the menu selection 3400 underneath the findings node and receives notice from Diagram Document that additional actions are required. The subject, Main Document, and the observers, Tree Menu and Edit Window, are now synchronized.

The observer, Tree Menu, executes the additional actions and the physician is next presented with a Locations menu 3402. The same interactions described above between the subject, Main Document, and the observers, Tree Menu and Edit Window, occur each time a menu is presented and selected by the physician. The physician makes a menu selection and in this example, the physician has selected a location of Mid-LAD Artery 3401. The observer, Tree Menu, observes the menu selection and informs the subject, Main Document, of the data change. Main Document may be uncoordinated with its observer's Tree Menu and Edit Window and informs them that they need to get coordinated. The observers react to this message and then query the subject, Main Document, for the change in data and the screen is refreshed with the data selected.

Figure 35:
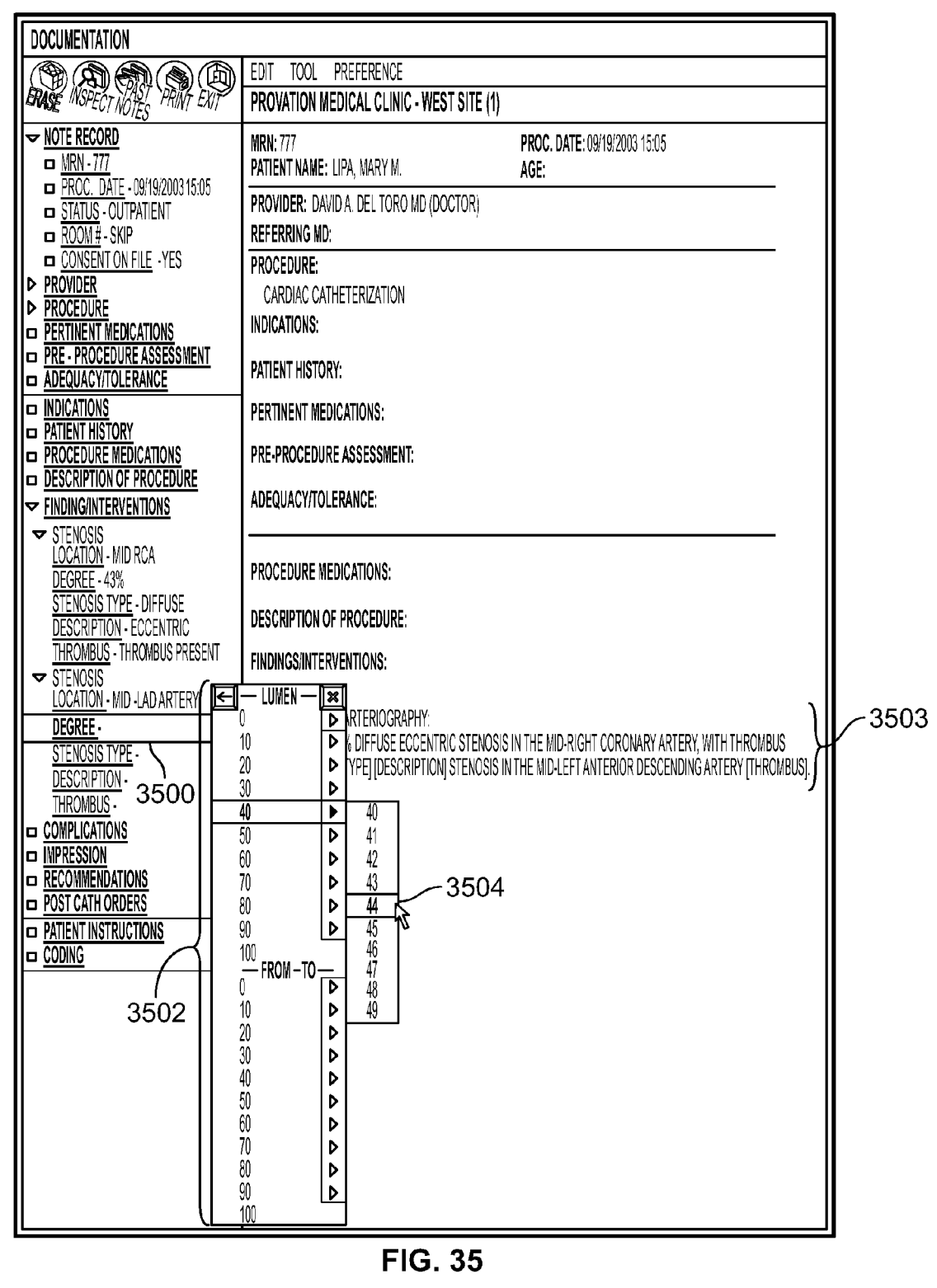

Referring to FIG. 35, the observer, Edit Window, displays the text string associated with a location 3503 and the observer, Tree Menu, displays the menu selection 3500 underneath the findings node and receives notice from Main Document that additional actions are required. The subject, Main Document, and the observers, Tree Menu and Edit Window, are now synchronized.

The observer, Tree Menu, executes the additional actions and the physician is next presented with a Degree menu 3502. The same interactions described above between the subject, Main Document, and the observers, Tree Menu and Edit Window, occur each time a menu is presented and selected by the physician. The physician makes a menu selection and in this example, the physician has selected a degree of 44 3504. The observer, Tree Menu, observes the menu selection and informs the subject, Main Document, of the data change. Main Document may be uncoordinated with its observer's Tree Menu and Edit Window and informs them that they need to get coordinated. The observers react to this message and then query the subject, Main Document, for the change in data and the screen is refreshed with the data selected Referring to FIG. 36, the observer, Edit Window, displays the text string associated with a degree 3603 and the observer, Tree Menu, displays the menu selection 3600 underneath the findings node and receives notice from Main Document that additional actions are required. The subject, Main Document, and the observers, Tree Menu and Edit Window, are now synchronized.

The observer, Tree Menu, executes the additional actions and the physician is next presented with a Stenosis Type menu 3602. The same interactions described above between the subject, Main Document and the observers, Tree Menu and Edit Window, occur each time a menu is presented and selected by the physician. The physician makes a menu selection and in this example, the physician has selected a Stenosis Type of Discrete 3604. The observer, Tree Menu, observes the menu selection and informs the subject, Main Document, of the data change. Main Document may be uncoordinated with its observer's Tree Menu and Edit Window and informs them that they need to get coordinated. The observers react to this message and then query the subject, Main Document, for the change in data and the screen is refreshed with the data selected.

Referring to FIG. 37, the observer, Edit Window, displays the text string associated with a stenosis type 3703 and the observer, Tree Menu, displays the menu selection 3700 underneath the findings node and receives notice from Main Document that additional actions are required. The subject, Main Document, and the observers, Tree Menu and Edit Window, are now synchronized.

The observer, Tree Menu, executes the additional actions and the physician is next presented with a Description menu 3702. The same interactions described above between the subject, Main Document, and the observers, Tree Menu and Edit Window, occur each time a menu is presented and selected by the physician. The physician makes a menu selection and in this example, the physician has selected a Description of Eccentric 3704. The observer, Tree Menu, observes the menu selection and informs the subject, Main Document, of the data change. Main Document may be uncoordinated with its observer's Tree Menu and Edit Window and informs them that they need to get coordinated. The observers react to this message and then query the subject, Main Document, for the change in data and the screen is refreshed with the data selected.

Referring to FIG. 38, the observer, Edit Window, displays the text string associated with a description 3803 and the observer, Tree Menu, displays the menu selection 3800 underneath the findings node and receives notice from Main Document that additional actions are required. The subject, Main Document, and the observers, Tree Menu and Edit Window, are now synchronized.

The observer, Tree Menu executes the additional actions and the physician is next presented with a Thrombus menu 3802. The same interactions described above between the subject, Main Document, and the observers, Tree Menu and Edit Window, occur each time a menu is presented and selected by the physician. The physician makes a menu selection and in this example, the physician has selected a Thrombus of Yes 3804. The observer, Tree Menu, observes the menu selection and informs the subject, Main Document, of the data change. Main Document may be uncoordinated with its observer's Tree Menu and Edit Window and informs them that they need to get coordinated. The observers react to this message and then query the subject, Main Document, for the change in data and the screen is refreshed with the data selected.

Referring to FIG. 39, the observer, Edit Window, displays the text string associated with a thrombus 3902 and the observer, Tree Menu, displays the menu selection 3900 underneath the findings node and receives notice from Main Document that no additional actions are required. The subject, Main Document, and the observers, Tree Menu and Edit Window, are now synchronized. The information displayed in the menu tree 3901 is consistent with the text displayed in the text window 3902 for both of the stenosis documented by the physician.

The physician's documenting of the findings via the menuing system has resulted in the creation of a synchronized diagram that has the stenosis correctly placed on the diagram given the information that was entered by the physician.

Referring to FIG. 40, the physician navigates to the Diagram Documentation menu selection 4002 and clicks on the menu item. After the physician selects the menu selection, Diagram Documentation 4002, the system stores the information stored in the Main Document subject and creates a new subject called Diagram Document and two observers called Diagram Tree Menu and Diagram Window. The system informs the subject, Diagram Document, of its observers and the subject is now in control of the application. Diagram Document calls its observers, Diagram Tree Menu and Diagram Window informing them that they need to get coordinated. After receiving this information from the subject the observers, Diagram Tree Menu and Diagram Window query the subject and retrieve the data that has changed.

The data retrieved by the observers is processed by the ontology inference engine. The ontology inference engine maps the data elements between the menu data elements and diagram data elements. This mapping enables the synchronization between the two disparate representations of data.

Figure 41:
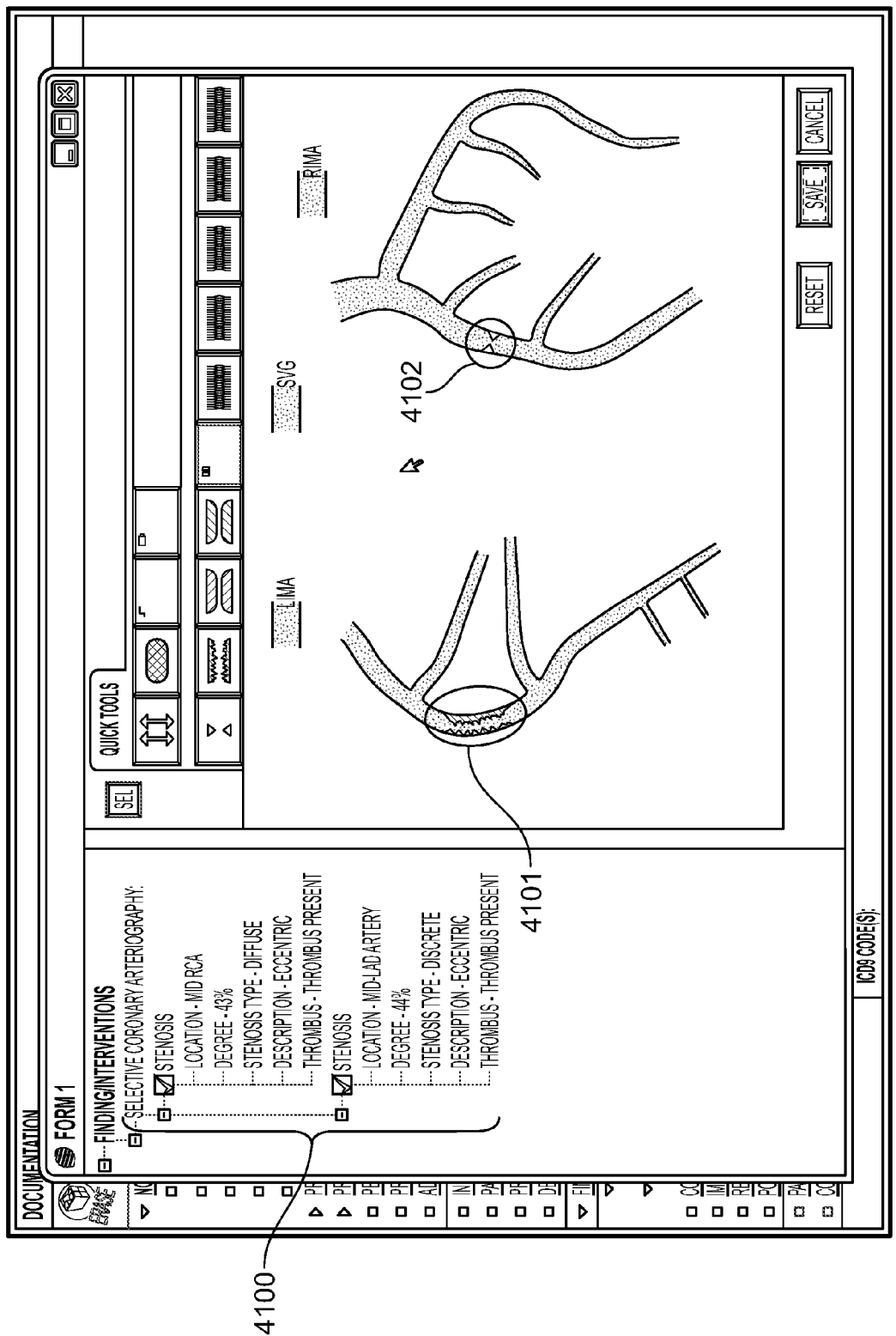
FIG. 41 is a screen shot illustrating the system's diagramming physician interface which shows the stenosis documented in the menu system displayed in the diagramming physician interface.

Referring now to FIG. 41, the observers, Diagram Tree Menu and Diagram Window, display the data which was retrieved from the Diagram Document subject. Diagram Document retrieved this data from the medical content database and the information associated with the selected patient. The data that was previously entered shows up in the inspection list 4100, a diffuse stenosis found in the Mid RCA artery 4101, and a discrete stenosis found in the Mid LAD artery 4102. The subject, Diagram Document, and its observers, Diagram Tree Menu and Diagram Window, are now synchronized and the physician is able to document additional findings via the Diagram Document subject if needed.

A system for the generating of naturally expressed medical procedure descriptions via a synchronized diagram and menu system has been described when documenting via the menu functionality. The procedure description documented in the menu where propagated and synchronized with the diagrams.

The description of invention demonstrates synchronization between the Findings of a Cardiac Catheterization procedure and a diagram but the invention is not limited to a specific section of the medical procedure description.

Figure 42:
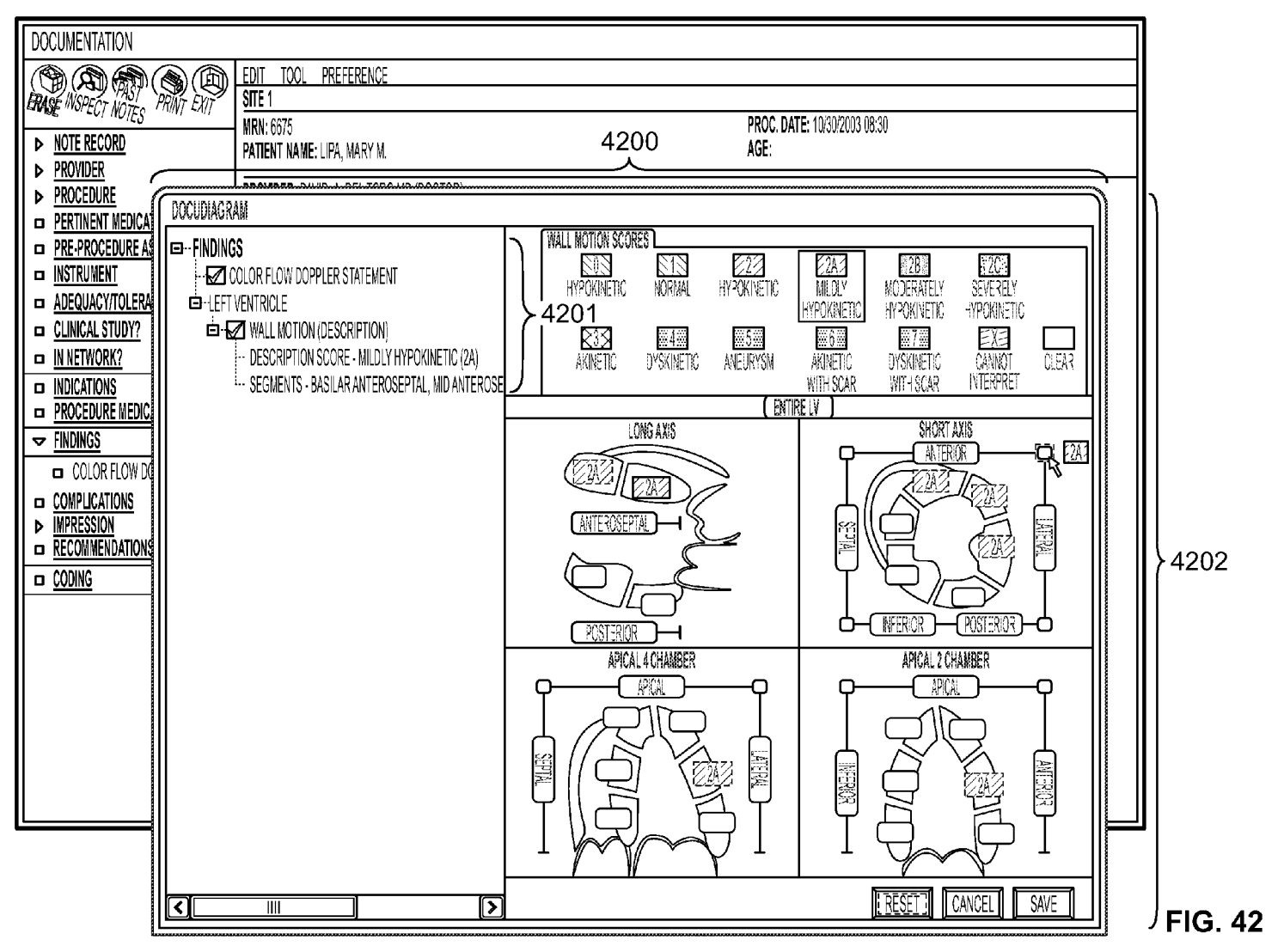

Referring to FIG. 42, the Echocardiography specialty has a need to document their medical procedure descriptions via a similar menu and diagram system. The invention has been implemented in the Echocardiography specialty with the same interaction model of the subject, Diagram Document 4200, and observers, Diagram Tree Menu 4201 and Diagram Window 4202. The invention is not limited to a specific medical specialty that completes medical procedure descriptions.

Those skilled in the art will recognize that the embodiments disclosed herein are exemplary in nature and that various changes can be made without departing from the scope and the spirit of this invention. Such various changes would become clear to one of ordinary skill in the art after inspection of the specification and the drawings. In that regard, as many changes as are possible to the embodiments of this invention utilizing the teachings thereof, the descriptions above, and the accompanying drawings should be interpreted in the illustrative and not the limited sense. The invention therefore is not to be restricted except within the spirit and scope of any appended claims.

The invention is by no means restricted to the embodiment shown. Many alternative versions are feasible in respect of the actual construction of the means used. The invention is not limited to procedure descriptions completed for procedures performed in Cardiology but in fact can be used to document procedures in any medical specialty. It should be noted that the invention is not restricted either to a special type of data, special configurations of data, programming languages, database systems, operating systems, or computing devices.

What is claimed is:

1. A method of documenting a medical procedure comprising:
    (a) generating an interface with at least one computing device including at least one database;
        wherein the interface includes a menu section including a plurality of menu data elements, the menu data elements being textual representations selectable to describe a medical procedure;
        wherein the interface includes a diagram window section including at least one graphical representation of an anatomical diagram illustrating at least part of a human body;

wherein the at least one database includes menu data elements mapped with graphical data elements;

(b) the at least one computing device receiving at least one menu input into the menu section of the interface selecting a menu data element reflecting at least part of the medical procedure;

(c) upon receipt of the at least one menu input, the at least one computing device automatically synchronizing the diagram window section with the menu section by:
  (i) accessing the at least one database and identifying with an ontology inference engine a graphical data element mapped with the selected at least one menu data element associated with the at least one menu input; and
  (ii) displaying in the diagram window section the identified graphical data element;

(d) the at least one computing device receiving at least one manipulation input into the diagram window section of the interface manipulating at least one graphical data element reflecting at least part of the medical procedure;

(e) upon receipt of the at least one manipulation input, the at least one computing device automatically synchronizing the menu section with the diagram window section by:
  (i) accessing the at least one database and identifying with an ontology inference engine at least one menu data element mapped with the manipulated graphical data element associated with the manipulation input; and
  (ii) displaying in the menu section an updated plurality of the identified menu data elements; and (f) upon each synchronization instance, the at least one computing device automatically constructing a concise textual medical procedure description based at least in part on one or more of the mapped menu data elements and the mapped graphical data elements to form at least one naturally expressed medical procedure description.

2. The method of claim 1, wherein said at least one computing device including at least one database further comprises a first database comprising medical content including a plurality of medical procedure descriptions, diagrams, and programming logic.

3. The method of claim 2, wherein said at least one computing device including at least one database further comprises a second database comprising a set of procedures terms and attributes representations.

4. The method of claim 3, wherein said at least one computing device comprises a plurality of computing devices, wherein the said interface, said first database and said second database operate on said plurality of said computing devices operating on a networked computing device system within a healthcare facility's wide area network.

5. The method of claim 4, wherein the said interface, said first database and said second database operate on said plurality of said computing devices operating on said networked computing device system within and outside of said healthcare facility's wide area network.

6. The method of claim 3, wherein said interface, said first database and said second database are distributed to said plurality of said computing devices operating on said networked computing device system within said healthcare facility's wide area network.

7. The method of claim 6, wherein said interface, said first database and said second database are distributed to said plurality of said computing devices operating on said networked computing device system within and outside of said healthcare facility's wide area network.

8. The method of claim 1, wherein the graphical representation of an anatomical diagram includes an illustration of an artery.

9. The method of claim 8, wherein the manipulation input received into the diagram window section identifies the location of a stenosis on the diagram of the artery.

10. A system for documenting medical procedure descriptions comprising:

(a) at least one computing device including at least one database generating an interface;
  wherein the interface includes a menu section including a plurality of menu data elements, the menu data elements being textual representations selectable to describe a medical procedure;
  wherein the interface includes a diagram window section including at least one graphical representation of an anatomical diagram illustrating at least part of a human body;
  wherein the at least one database includes menu data elements mapped with graphical data elements;

(b) the at least one computing device programmed to receive at least one menu input into the menu section of the interface selecting a menu data element reflecting at least part of the medical procedure;

(c) the at least one computing device programmed to automatically synchronize the diagram window section with the menu section upon receipt of the at least one menu input, wherein the at least one computing device is programmed to:
  (i) access the at least one database and identify with an ontology inference engine a graphical data element mapped with the selected at least one menu data element associated with the at least one menu input; and
  (ii) display in the diagram window section the identified graphical data element;

(d) the at least one computing device programmed to receive at least one manipulation input into the diagram window section of the interface manipulating at least one graphical data element reflecting at least part of the medical procedure;

(e) the at least one computing device programmed to automatically synchronize the menu section with the diagram window section upon receipt of the at least one manipulation input, wherein the at least one computing device is programmed to:
  (i) access the at least one database and identify with an ontology inference engine at least one menu data element mapped with the manipulated graphical data element associated with the manipulation input; and
  (ii) display in the menu section an updated plurality of the identified menu data elements; and (f) the at least one computing device programmed to, upon each synchronization instance, automatically construct a concise textual medical procedure description based at least in part on one or more of the mapped menu data elements and the mapped graphical data elements to form at least one naturally expressed medical procedure description.

11. The system of claim 10, wherein said at least one computing device including at least one database further comprises a first database comprising medical content including a plurality of medical procedure descriptions, diagrams, and programming logic.

12. The system of claim 11, wherein said at least one computing device including at least one database further comprises a second database comprising a set of procedures terms and attributes representations.

13. The system of claim 12, wherein said at least one computing device comprises a plurality of computing devices, wherein the said interface, said first database and said second database operate on said plurality of said computing devices operating on a networked computing device system within a healthcare facility's wide area network.

14. The system of claim 13, wherein the said interface, said first database and said second database operate on said plurality of said computing devices operating on said networked computing device system within and outside of said healthcare facility's wide area network.

15. The system of claim 12, wherein said interface, said first database and said second database are distributed to said plurality of said computing devices operating on said networked computing device system within said healthcare facility's wide area network.

16. The system of claim 15, wherein said interface, said first database and said second database are distributed to said plurality of said computing devices operating on said networked computing device system within and outside of said healthcare facility's wide area network.

17. The system of claim 10, wherein the graphical representation of an anatomical diagram includes an illustration of an artery.

18. The system of claim 17, wherein the manipulation input received into the diagram window section identifies the location of a stenosis on the diagram of the artery.

* * * * *